United States Patent
Kase et al.

(10) Patent No.: US 11,974,499 B2
(45) Date of Patent: Apr. 30, 2024

(54) ORGANIC EL DEVICE, AMINE COMPOUND HAVING BENZAZOLE RING STRUCTURE, AND METHOD IN WHICH SAID AMINE COMPOUND IS USED IN CAPPING LAYER OF ORGANIC EL DEVICE

(71) Applicant: HODOGAYA CHEMICAL CO., LTD., Tokyo (JP)

(72) Inventors: Kouki Kase, Tokyo (JP); Takeshi Yamamoto, Tokyo (JP); Shunji Mochizuki, Tokyo (JP); Shuichi Hayashi, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 949 days.

(21) Appl. No.: 16/959,734

(22) PCT Filed: Jan. 10, 2019

(86) PCT No.: PCT/JP2019/000452
§ 371 (c)(1),
(2) Date: Jul. 2, 2020

(87) PCT Pub. No.: WO2019/139065
PCT Pub. Date: Jul. 18, 2019

(65) Prior Publication Data
US 2020/0365809 A1   Nov. 19, 2020

(30) Foreign Application Priority Data

Jan. 10, 2018 (JP) ................ 2018-001564

(51) Int. Cl.
*H10K 85/60* (2023.01)
*H10K 50/15* (2023.01)
(Continued)

(52) U.S. Cl.
CPC ........ *H10K 85/654* (2023.02); *H10K 85/631* (2023.02); *H10K 50/15* (2023.02); *H10K 50/16* (2023.02); *H10K 50/171* (2023.02)

(58) Field of Classification Search
CPC ... C07D 249/18; C07D 249/20; H10K 85/636
See application file for complete search history.

(56) References Cited

U.S. PATENT DOCUMENTS

| | | | |
|---|---|---|---|
| 5,639,914 | A | 6/1997 | Tomiyama et al. |
| 5,707,747 | A | 1/1998 | Tomiyama et al. |

(Continued)

FOREIGN PATENT DOCUMENTS

| | | |
|---|---|---|
| EP | 3432688 A1 | 1/2019 |
| JP | H08-48645 A | 2/1996 |

(Continued)

OTHER PUBLICATIONS

Written Opinion dated Apr. 9, 2019 in PCT/JP2019/000452 filed Jan. 10, 2019, 11 pages (with English translation).

(Continued)

*Primary Examiner* — Vu A Nguyen
(74) *Attorney, Agent, or Firm* — Birch, Stewart, Kolasch & Birch, LLP

(57) ABSTRACT

The present invention relates to an organic EL device having at least an anodic electrode, a hole transport layer, a light emitting layer, an electron transport layer, a cathodic electrode, and a capping layer in this order, in which the capping layer contains an amine compound having a benzazole ring structure represented by the following general formula (A-1).

(Continued)

← 9 Capping layer
← 8 Cathode
← 7 Electron injection layer
← 6 Electron transport layer
← 5 Light emitting layer
← 4 Hole transport layer
← 3 Hole injection layer
← 2 Transparent anode
← 1 Glass substrate

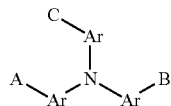

(A-1)

13 Claims, 1 Drawing Sheet

(51) Int. Cl.
*H10K 50/16* (2023.01)
*H10K 50/17* (2023.01)

(56) References Cited

U.S. PATENT DOCUMENTS

| 5,792,557 | A | 8/1998 | Nakaya et al. | |
|---|---|---|---|---|
| 11,056,653 | B2 * | 7/2021 | Yokoyama | H10K 85/657 |
| 2013/0074927 | A1 | 3/2013 | Rachwal et al. | |
| 2014/0225100 | A1 | 8/2014 | Yokoyama et al. | |
| 2017/0186976 | A1 | 6/2017 | Tanabe et al. | |
| 2018/0114925 | A1 | 4/2018 | Tanabe et al. | |
| 2019/0115542 | A1 | 4/2019 | Yokoyama et al. | |

FOREIGN PATENT DOCUMENTS

| JP | 3194657 | B2 | 7/2001 | |
|---|---|---|---|---|
| JP | 2002151268 | A | 5/2002 | |
| JP | 2003068464 | A | 3/2003 | |
| JP | 2013072087 | A | 4/2013 | |
| JP | 2016-86147 | A | 5/2016 | |
| JP | 2017191661 | A | 10/2017 | |
| KR | 100861168 | B1 | 9/2008 | |
| KR | 10-20170116927 | A | 10/2017 | |
| TW | 201602094 | A | 1/2016 | |
| WO | WO-2013038627 | A1 | 3/2013 | |
| WO | WO-2014009310 | A1 | 1/2014 | |
| WO | WO-2015001726 | A1 | 1/2015 | |
| WO | WO 2017/011531 | A2 | 1/2017 | |
| WO | WO-2017183625 | A1 * | 10/2017 | C07B 61/00 |

OTHER PUBLICATIONS

Office Action and Search Report dated Oct. 25, 2022 in Chinese Patent Application No. 201980008139.1 (with English translation), 15 pages.
Office Action dated Nov. 15, 2022 in Japanese Patent Application No. 2019-564725 (with English translation), 5 pages.
Ayataka Endo, et al, "Efficient up-conversion of triplet excitons into a singlet state and its application for organic light emitting diodes", Applied Physics Letters, 98, 2011, pp. 083302-1-083302-3.
Chishio Hosokawa et al, "Development of styryl-based light-emitting materials", Japan Society of Applied Physics, 9th Class, Proceedings, 2001, pp. 55 to 61.
H. Riel, et al, "Phosphorescent top-emitting organic light-emitting devices with improved light outcoupling", Applied Physics Letters, vol. 82, No. 3, Jan. 20, 2003, pp. 466-468.
International Search Report dated Apr. 9, 2019 in PCT/JP2019/000452 (with English translation), 5 pages.
L.S. Hung, et al, "Application of an ultrathin LiF/Al bilayer in organic surface-emitting diodes", Applied Physics Letters, vol. 78, No. 4, Jan. 22, 2001, pp. 544-546.
Leonard K. Dyall, et al, "Oxidative Cyclizations. VIII* Mechanisms of Oxidation of ortho-Substituted Benzenamines and Improved Cyclizations by Bis(acetato-O)phenyliodine", Aust. J. Chem., 45, 1992, pp. 371-384.
N. Miyaura, et al, "The Palladium-Catalyzed Cross-Coupling Reaction of Phenylboronic Acid with Halorenes in the Presence of Bases", Synthetic Communications, 11(7), 1981, pp. 513-519.
Tatsuo Ishiyama, et al, "Palladium(0)-Catalyzed Cross-Coupling Reaction of Alkoxydiboron with Halorenes: A Direct Procedure for Arylboronic Esters", J. Org. Chem., 60, 1995, pp. 7508-7510.
Japanese Office Action dated Aug. 9, 2022 in Patent Application No. 2019-564725 (with English translation), 5 pages.
Office Action dated Aug. 1, 2022 in Taiwanese Patent Application No. 108100997 (with English translation), 7 pages.
Extended European Search Report dated Sep. 10, 2021 in Patent Application No. 19738462.1, 7 pages.
Japanese Office Action for Japanese Application No. 2019-564725, dated Mar. 14, 2023, with an English translation.
Korean Office Action for Korean Application No. 10-2020-7019216, dated Dec. 8, 2023, with English translation.
Taiwanese Office Action and Search Report for corresponding Taiwanese Application No. 108100997, dated Nov. 16, 2023, with English translation.

* cited by examiner

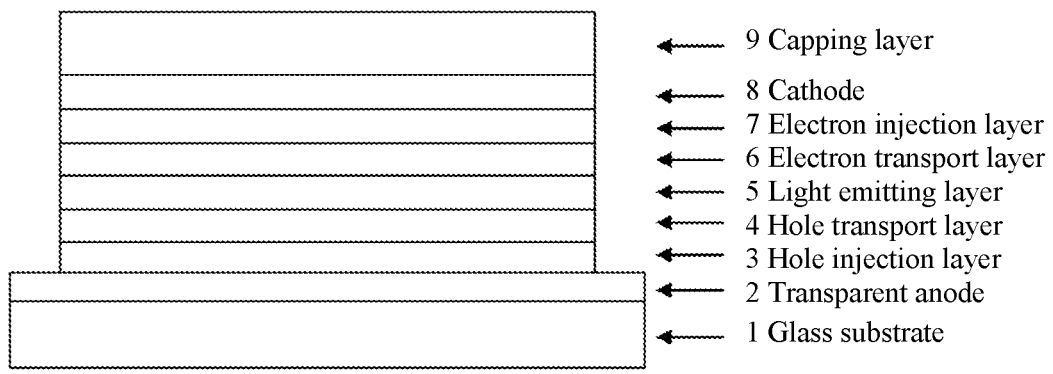

ORGANIC EL DEVICE, AMINE COMPOUND HAVING BENZAZOLE RING STRUCTURE, AND METHOD IN WHICH SAID AMINE COMPOUND IS USED IN CAPPING LAYER OF ORGANIC EL DEVICE

TECHNICAL FIELD

The present invention relates to a compound and a device suitable for an organic electroluminescence device (hereinafter abbreviated as an organic EL device) which is a light emitting device suitable for various display devices, specifically relates to a compound having a benzazole ring structure, an organic EL device using the compound and a method of using the compound in an organic EL device.

BACKGROUND ART

Since organic EL devices are self-luminescent devices, they are bright and excellent in visibility as compared with liquid-crystalline devices, and capable of giving clear display. Therefore, the organic EL devices have been actively studied.

In 1987, C. W. Tang et al. of Eastman Kodak Company put an organic EL device using organic materials into practical use by developing a device having a multilayered structure in which various roles are assigned to respective materials. They formed a lamination of a fluorescent material capable of transporting electrons and an organic material capable of transporting holes, so that both charges are injected into the layer of the fluorescent material to emit light, thereby achieving a high luminance of 1,000 cd/m$^2$ or more at a voltage of 10 V or lower (see, for example, Patent Literatures 1 and 2).

To date, many improvements have been performed for practical utilization of the organic EL devices. And in an electroluminescent device in which an anode, a hole injection layer, a hole transport layer, a light emitting layer, an electron transport layer, an electron injection layer, and a cathode are sequentially provided on a substrate, to further subdivide various roles of the multilayered structure, high efficiency and high durability have been achieved by a light emitting device having a bottom emission structure that emits light from a bottom portion (see, for example, Non-Patent Literature 1).

In recent years, a light emitting device having a top emission structure that uses a metal having a high work function as an anode and emits light from an upper portion has been used. In the bottom emission structure in which light is extracted from a bottom portion having a pixel circuit, the area of the light emitting portion is limited. On the other hand, in the light emitting device having the top emission structure, since light is extracted from the upper portion, there is an advantage that the light emitting portion can be widened without blocked by the pixel circuit. In the light emitting device having a top emission structure, a translucent electrode such as LiF/Al/Ag (see, for example, Non-Patent Literature 2), Ca/Mg (see, for example, Non-Patent Literature 3), or LiF/MgAg is used as a cathode.

In such a light emitting device, in the case where light emitted on the light emitting layer is incident on another film, when incident at a certain angle or above, light is totally reflected at an interface between the light emitting layer and the other film. Therefore, only a part of the emitted light was available. In recent years, in order to improve light extraction efficiency, a light emitting device in which a "capping layer" having a high refractive index is provided outside the translucent electrode having a low refractive index has been proposed (see, for example, Non-Patent Literatures 2 and 3).

An effect of the capping layer in the light emitting device having a top emission structure is: in the light emitting device using Ir(ppy)3 as a light emitting material, current efficiency was 38 cd/A in the case where there was no capping layer; whereas in a light emitting device using ZnSe having a film thickness of 60 nm as the capping layer, current efficiency was 64 cd/A and efficiency improvement of about 1.7 times was recognized. It has been also shown that a maximum point of transmittance of the translucent electrode and the capping layer does not necessarily coincide with a maximum point of efficiency, and it has been shown that a maximum point of light extraction efficiency is determined by an interference effect (see, for example, Non-Patent Literature 3).

Conventionally, it has been proposed to use a metal mask having high definition to form of the capping layer, but in use under high temperature conditions, there is a problem that alignment accuracy decreases since distortion due to heat occurs in the metal mask. Therefore, since ZnSe has a melting point as high as 1,100° C. or higher (see, for example, Non-Patent Literature 3), it cannot be deposited at a correct position by a metal mask having high definition, and thus may affect the light emitting device itself. Further, since film formation by a sputtering method also affects the light emitting device, the capping layer containing an inorganic substance as a constituent material is not suitable for use.

In addition, in the case where tris(8-hydroxyquinoline) aluminum (hereinafter abbreviated as Alq$_3$) is used as the capping layer for adjusting a refractive index (see, for example, Non-Patent Literature 2), Alq$_3$ is known as an organic EL material commonly used as a green light emitting material or an electron transport material, but has weak absorption near 450 nm used as a blue light emitting material, so that there is a problem of reduction in color purity and reduction in light extraction efficiency in the case of a blue light emitting device.

In a device produced by using a conventional capping layer, since among sunlight, light having a wavelength of 400 nm to 410 nm may pass therethrough and affect a material inside the device, there is also a problem of reduction in color purity and reduction in light extraction efficiency.

In order to improve device characteristics of the organic EL device, in particular, in order to absorb light having a wavelength of 400 nm to 410 nm among sunlight not to affect the material inside the device and considerably improve light extraction efficiency, a material having a high light absorption coefficient, a high refractive index, and excellent stability or durability of a thin film is demanded as a material of the capping layer.

CITATION LIST

Patent Literature

Patent Literature 1: JP-A-H08-048656
Patent Literature 2: Japanese Patent No. 3194657
Patent Literature 3: WO 2014/009310
Patent Literature 4: WO 2013/038627

Non-Patent Literature

Non-Patent Literature 1: Japan Society of Applied Physics, 9th Class, Proceedings, Pages 55 to 61 (2001)
Non-Patent Literature 2: Appl. Phys. Let., 78, 544 (2001)
Non-Patent Literature 3: Appl. Phys. Let., 82, 466 (2003)
Non-Patent Literature 4: Aust. J. Chem., 45, 371 (1992)
Non-Patent Literature 5: J. Org. Chem., 60, 7508 (1995)
Non-Patent Literature 6: Synth. Commun., 11, 513 (1981)
Non-Patent Literature 7: Appl. Phys. Lett., 98, 083302 (2011)

SUMMARY OF INVENTION

Technical Problem

In order to improve device characteristics of an organic EL device, in particular, in order to absorb light having a wavelength of 400 nm to 410 nm among sunlight not to affect the material inside the device and considerably improve light extraction efficiency, an object of the present invention is to provide an organic EL device including a capping layer constituted by a material having (1) a high light absorption coefficient, (2) a high refractive index, (3) good stability in a thin film, (4) excellent durability, (5) excellent light resistance, and (6) no absorption in each wavelength range of blue, green and red.

Physical characteristics of the material of the capping layer suitable for the present invention can include (1) a high light absorption coefficient, (2) a high refractive index, (3) capable of deposition, (4) a stable thin film state, and (5) a high glass transition temperature. Physical characteristics of the device suitable for the present invention can include (1) absorption of light from 400 nm to 410 nm, (2) high light extraction efficiency, (3) no reduction in color purity, (4) transmission of light without change over time, and (5) a long lifetime.

Solution to Problem

Therefore, in order to achieve the above object, the present inventors focused on the fact that aryl amine materials have excellent stability and durability of a thin film, and screened materials having a high absorbance at a wavelength of 400 nm to 410 nm in an absorption spectrum of a concentration of $10^{-5}$ mol/L regarding amine compounds having a specific benzazole ring structure with a high refractive index. They produced organic EL devices using the materials as a material constituting the capping layer, and characteristics of the device were evaluated earnestly. As a result, they have completed the present invention.

That is, according to the present invention, the following organic EL device is provided.

An organic EL device having at least an anodic electrode, a hole transport layer, a light emitting layer, an electron transport layer, a cathodic electrode, and a capping layer in this order, in which the capping layer contains an amine compound having a benzazole ring structure represented by the following general formula (A-1).

[Chem. 1]

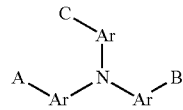

(A-1)

(In the formula, A represents a monovalent group represented by the following general formula (B-1) where one position in $R_1$ to $R_6$ is a bonding site; B and C may be the same as or different from each other, and each represents a monovalent group represented by the following general formula (B-1) where one position in $R_1$ to $R_6$ is a bonding site, a substituted or unsubstituted aromatic hydrocarbon group, a substituted or unsubstituted aromatic heterocyclic group, or a substituted or unsubstituted condensed polycyclic aromatic group; Ar's may be the same as or different from each other, and each represents a divalent group of a substituted or unsubstituted aromatic hydrocarbon group, a substituted or unsubstituted aromatic heterocyclic group, or a substituted or unsubstituted condensed polycyclic aromatic group, or a single bond. Ar's adjacent to each other via a nitrogen atom may be bonded by a single bond, a substituted or unsubstituted methylene group, an oxygen atom, or a sulfur atom to form a ring.)

[Chem. 2]

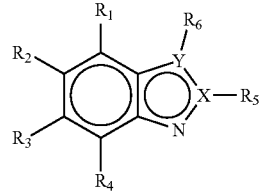

(B-1)

(In the formula, $R_1$ to $R_6$ may be the same as or different from each other, and each represents a linking group as a bonding site, a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; and X and Y represent a carbon atom or a nitrogen atom. However, in the case where X and Y are nitrogen atoms, X or Y does not have $R_5$ or $R_6$, and the case where X and Y are carbon atoms is excepted.)

According to the present invention, there is provided an amine compound having a benzazole ring structure represented by the following general formula (A-1).

[Chem. 3]

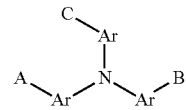

(A-1)

(In the formula, A represents a monovalent group represented by the following general formula (B-1) where one position in $R_1$ to $R_6$ is a bonding site; B and C may be the same as or different from each other, and each represents a monovalent group represented by the following general formula (B-1) where one position in $R_1$ to $R_6$ is a bonding site, a substituted or unsubstituted aromatic hydrocarbon group, a substituted or unsubstituted aromatic heterocyclic group, or a substituted or unsubstituted condensed polycyclic aromatic group; Ar's may be the same as or different from each other, and each represents a divalent group of a substituted or unsubstituted aromatic hydrocarbon group, a substituted or unsubstituted aromatic heterocyclic group, or a substituted or unsubstituted condensed polycyclic aromatic group, or a single bond. Ar's adjacent to each other via a nitrogen atom may be bonded by a single bond, a substituted or unsubstituted methylene group, an oxygen atom, or a sulfur atom to form a ring.)

[Chem. 4]

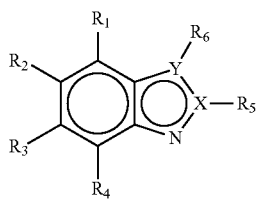

(B-1)

(In the formula, $R_1$ to $R_6$ may be the same as or different from each other, and each represents a linking group as a bonding site, a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; and X and Y represent a carbon atom or a nitrogen atom. However, in the case where X and Y are nitrogen atoms, X or Y does not have $R^5$ or $R^6$, and the case where X and Y are carbon atoms is excepted.)

Advantageous Effects of Invention

Since the organic EL device of the present invention has a capping layer which is provided outside the transparent or translucent electrode and has a refractive index higher than that of the translucent electrode, it is possible to obtain an organic EL device capable of significantly improving light extraction efficiency. In addition, since an amine compound having a benzazole ring compound represented by the general formula (A-1) is used in the capping layer, film formation can be performed at a temperature of not higher than 400° C., and thus the present invention can optimize light extraction efficiency of each color by using a high definition mask without damaging the light emitting device, can be suitably applied to a full color display, and can display a clear and bright image with high color purity.

Since the organic EL device of the present invention uses, as a material of the capping layer, an organic EL device material having a high light absorption coefficient, a high refractive index, excellent stability, durability and light resistance of a thin film, it is possible to maintain color purity and significantly improve light extraction efficiency without being affected by sunlight, as compared with a conventional organic EL device. Further, it is possible to realize an organic EL device having high efficiency and a long life.

BRIEF DESCRIPTION OF DRAWING

FIG. 1 This is a diagram illustrating an organic EL device configuration of Examples 17 to 29 and Comparative Examples 1 and 2.

DESCRIPTION OF EMBODIMENTS

An embodiment of the present invention will be described in detail below. First, aspects of the present embodiment will be listed and described. In the present application, a term "to" is a term representing a range. For example, description of "5 to 10" means "5 or more and 10 or less", and represents a range including numerical values themselves described before and after "to".

1) An organic EL device having at least an anodic electrode, a hole transport layer, a light emitting layer, an electron transport layer, a cathodic electrode, and a capping layer in this order, in which the capping layer contains an amine compound having a benzazole ring structure represented by the following general formula (A-1).

[Chem. 5]

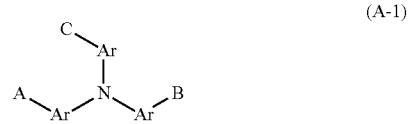

(A-1)

(In the formula, A represents a monovalent group represented by the following general formula (B-1) where one position in $R_1$ to $R_6$ is a bonding site; B and C may be the same as or different from each other, and each represents a monovalent group represented by the following general formula (B-1) where one position in $R_1$ to $R_6$ is a bonding site, a substituted or unsubstituted aromatic hydrocarbon group, a substituted or unsubstituted aromatic heterocyclic group, or a substituted or unsubstituted condensed polycyclic aromatic group; Ar's may be the same as or different from each other, and each represents a divalent group of a substituted or unsubstituted aromatic hydrocarbon group, a substituted or unsubstituted aromatic heterocyclic group, or a substituted or unsubstituted condensed polycyclic aromatic group or a single bond. Ar's adjacent to each other via a nitrogen atom may be bonded by a single bond, a substituted or unsubstituted methylene group, an oxygen atom, or a sulfur atom to form a ring.)

[Chem. 6]

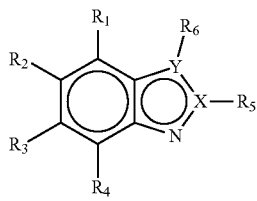

(B-1)

(In the formula, $R_1$ to $R_6$ may be the same as or different from each other, and each represents a linking group as a bonding site, a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; and X and Y represent a carbon atom or a nitrogen atom. However, in the case where X and Y are nitrogen atoms, X or Y does not have $R^5$ or $R^6$, and the case where X and Y are carbon atoms is excepted.)

2) The organic EL device according to 1), in which the amine compound having a benzazole ring structure has an extinction coefficient of 0.20 or more at a wavelength of 400 nm to 410 nm and has an absorbance of 0.20 or more at a wavelength of 400 nm to 410 nm in an absorption spectrum of a toluene solution with a concentration of $1.0\times10^{-5}$ mol/L.

3) The organic EL device according to 1), in which the general formula (B-1) is represented by the following general formula (B-2) or (B-3).

[Chem. 7]

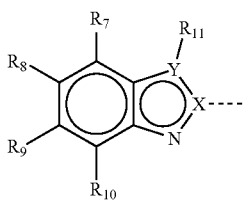

(B-2)

[Chem. 8]

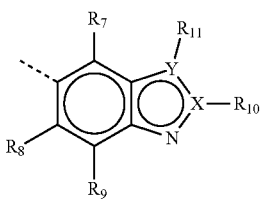

(B-3)

(In the formulae, a broken line is a bonding site, $R_7$ to $R_{11}$ may be the same as or different from each other, and each represents a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; and X and Y represent a carbon atom or a nitrogen atom. However, in the case where X and Y are nitrogen atoms, Y does not have $R_{11}$, and the case where X and Y are carbon atoms is excepted.)

4) The organic EL device according to 1), in which the general formula (B-1) is represented by the following general formula (B-4) or (B-5).

[Chem. 9]

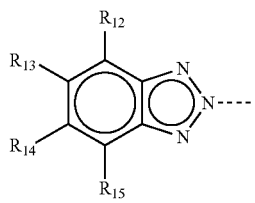

(B-4)

[Chem. 10]

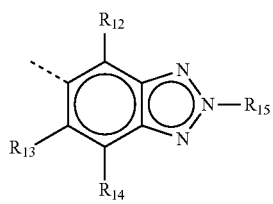

(B-5)

(In the formulae, a broken line is a bonding site, $R_{12}$ to $R_{15}$ may be the same as or different from each other, and each represents a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group.)

5) The organic EL device according to any one of 1) to 4), in which A, B and C each have a benzazole ring structure in the general formula (A-1).

6) The organic EL device according to any one of 1) to 4), in which in the general formula (A-1), A and B each have a benzazole ring structure, and C represents a substituted or unsubstituted aromatic hydrocarbon group, a substituted or unsubstituted aromatic heterocyclic group, or a substituted or unsubstituted condensed polycyclic aromatic group.

7) The organic EL device according to any one of 1) to 4), in which in the general formula (A-1), A has a benzazole ring structure, and B and C each represents a substituted or unsubstituted aromatic hydrocarbon group, a substituted or unsubstituted aromatic heterocyclic group, or a substituted or unsubstituted condensed polycyclic aromatic group.

8) The organic EL device according to 1), in which A, B and C are the same as each other in the general formula (A-1).

9) The organic EL device according to 5) or 6), in which A and B are the same as each other in the general formula (A-1).

10) The organic EL device according to any one of 5) to 7), in which A, B and C are not the same as each other in the general formula (A-1).

11) The organic EL device according to any one of 5) to 7), in which A and B are not the same as each other in the general formula (A-1).

12) The organic EL device according to 1), in which the capping layer has a thickness in a range of 30 nm to 120 nm.

13) The organic EL device according to 1), in which the capping layer has a refractive index of 1.85 or more with respect to light having a wavelength in a range of 400 nm to 410 nm.

14) A method of using an amine compound having a benzotriazole ring structure where A or B in the general formula (A-1) as described in 1) is represented by the general formula (B-4) or (B-5) as described in 4), in a capping layer of an organic EL device.

15) An amine compound having a benzazole ring structure represented by the following general formula (A-1).

[Chem. 11]

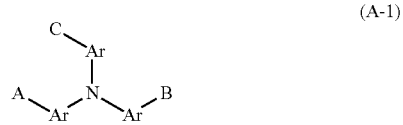

(A-1)

(In the formula, A represents a monovalent group represented by the following general formula (B-1) where one position in $R_1$ to $R_6$ is a bonding site; B and C may be the same as or different from each other, and each represents a monovalent group represented by the following general formula (B-1) where one position in $R_1$ to $R_6$ is a bonding site, a substituted or unsubstituted aromatic hydrocarbon group, a substituted or unsubstituted aromatic heterocyclic group, or a substituted or unsubstituted condensed polycyclic aromatic group; Ar's may be the same as or different from each other, and each represents a divalent group of a substituted or unsubstituted aromatic hydrocarbon group, a substituted or unsubstituted aromatic heterocyclic group, or a substituted or unsubstituted condensed polycyclic aromatic group, or a single bond. Ar's adjacent to each other via a nitrogen atom may be bonded by a single bond, a substituted or unsubstituted methylene group, an oxygen atom, or a sulfur atom to form a ring.)

[Chem. 12]

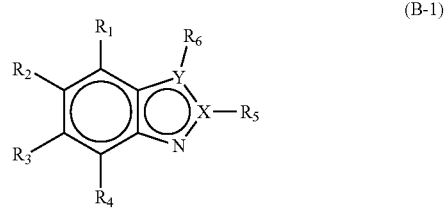

(B-1)

(In the formula, $R_1$ to $R_6$ may be the same as or different from each other, and each represents a linking group as a bonding site, a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; and X and Y represent a carbon atom or a nitrogen atom. However, in the case where X and Y are nitrogen atoms, X or Y does not have $R_5$ or $R_6$, and the case where X and Y are carbon atoms is excepted.)

The "aromatic hydrocarbon group", the "aromatic heterocyclic group" or the "condensed polycyclic aromatic group" in the "substituted or unsubstituted aromatic hydrocarbon group", the "substituted or unsubstituted aromatic heterocyclic group" or the "substituted or unsubstituted condensed polycyclic aromatic group", which is represented by B, C, Ar, and $R_1$ to $R_{15}$ in the general formulae (A-1), (B-1), (B-2), (B-3), (B-4), and (B-5), is specifically selected from a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, a triphenylenyl group, a pyridyl group, a pyrimidinyl group, a thoriadinyl group, a furyl group, a pyrrolyl group, a thienyl group, a quinolyl group, a isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, a carborinyl group, and the like, and an aryl group having a carbon number of 6 to 30 or a heteroaryl group having a carbon number of 2 to 20.

As the "linear or branched alkyl group having a carbon number of 1 to 6", the "cycloalkyl group having a carbon number of 5 to 10", the "linear or branched alkenyl group having a carbon number of 2 to 6", the "linear or branched alkyloxy group having a carbon number of 1 to 6", the "cycloalkyloxy group having a carbon number of 5 to 10", or the "aryloxy group" in the "linear or branched alkyl group having a carbon number of 1 to 6 which may have a substituent", the "cycloalkyl group having a carbon number of 5 to 10 which may have a substituent", the "linear or branched alkenyl group having a carbon number of 2 to 6 which may have a substituent", the "linear or branched alkyloxy group having a carbon number of 1 to 6 which may have a substituent", the "cycloalkyloxy group having a carbon number of 5 to 10 which may have a substituent", or the "substituted or unsubstituted aryloxy group", which is represented by $R_1$ to $R_{15}$ in the general formulae (B-1), (B-2), (B-3), (B-4), and (B-5), specific examples thereof include a methyl group, an ethyl group, an n-propyl group, an isopropyl group, an n-butyl group, an isobutyl group, a tert-butyl group, an n-pentyl group, an isopentyl group, a neopentyl group, an n-hexyl group, and a cyclopentyl group, a cyclohexyl group, a 1-adamantyl group, a 2-adamantyl group, a vinyl group, an allyl group, an isopropenyl group, a 2-butenyl group, a methyloxy group, an ethyloxy group, an n-propyloxy group, a cyclopentyloxy group, a cyclohexyloxy group, a 1-adamantyloxy group, a phenyloxy group, a tolyloxy group, a biphenyloxy group, and the like.

As the "substituent" in the "substituted aromatic hydrocarbon group", the "substituted aromatic heterocyclic group", the "substituted condensed polycyclic aromatic group", the "linear or branched alkyl group having a carbon number of 1 to 6 which may have a substituent", the "cycloalkyl group having a carbon number of 5 to 10 which may have a substituent the a "linear or branched alkenyl group having a carbon number of 2 to 6 which may have a substituent", the "linear or branched alkyloxy group having a carbon number of 1 to 6 which may have a substituent", the "cycloalkyloxy group having a carbon number of 5 to 10 which may have a substituent", the "substituted aryloxy group", or the "substituted methylene group", which is represented by B, C, Ar, and $R_1$ to $R_{15}$ in the general formulae (A-1), (B-1), (B-2), (B-3), (B-4), and (B-5), specific examples thereof include a deuterium atom, a cyano group, a nitro group; halogen atoms such as a fluorine atom, a chlorine atom, a bromine atom, and an iodine atom; silyl groups such as a trimethyl silyl group and a triphenyl silyl group; a linear or branched alkyl group having a carbon number of 1 to 6 such as a methyl group, an ethyl group, and a propyl group; a linear or branched alkyloxy group having a carbon number of 1 to 6 such as a methyloxy group, an ethyloxy group, and a propyloxy group; alkenyl groups such as a vinyl group and an allyl group; aryloxy groups such as a phenyloxy group and a tolyloxy group; aryl alkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, a spirobifluorenyl group, an indenyl group, a pyrenyl group, a perylenyl group, a fluoranthenyl group, and a triphenylenyl group; a pyridyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, and a benzothiazolyl group, a quinoxalinyl group, a benzoimidazolyl group, a pyrazolyl group, a dibenzofuranyl group, a dibenzothienyl group, and a carborinyl group, and an aryl group having a carbon number of 6 to 30 or a heteroaryl group having a carbon number of 2 to 20, and these substituents may be further substituted with the exemplified substituents. In addition, the substituent and the substituted benzene ring or plurality of substituents substituted with the same benzene ring may be bonded to each other via a single bond, a substituted or unsubstituted methylene group, an oxygen atom, or a sulfur atom to form a ring.

In the organic EL device of the present embodiment, Ar in the general formula (A-1) is preferably a substituted or unsubstituted aromatic hydrocarbon group, and more preferably a substituted or unsubstituted phenyl group.

Further, in the organic EL device of the present embodiment, the thickness of the capping layer is preferably in a range of 30 nm to 120 nm and more preferably in a range of 40 nm to 80 nm.

In the organic EL device of the present embodiment, the refractive index of the capping layer with respect to light having a wavelength in a range of 400 nm to 410 nm is preferably 1.85 or more and more preferably 1.90 or more.

In the organic EL device of the present embodiment, the capping layer may be produced by laminating or mixing two or more kinds of different constituent materials.

The amine compound having the benzazole ring structure represented by the general formula (A-1) of the present embodiment is a new compound, and a benzazole derivative which is a main skeleton of these compounds can be synthesized by a per se known method, for example, as follows (for example, see Non-Patent Literature 4). Further, by performing a coupling reaction of the synthesized halogenated benzazole derivative and an aryl amine by using a copper catalyst, a palladium catalyst or the like, the amine compound having a benzazole ring structure represented by the general formula (A-1) of the present embodiment can be synthesized. In addition, also by converting the halogenated benzazole derivative to a boronic acid derivative or a boronic acid ester derivative, the amine compound having a benzazole ring structure represented by the general formula (A-1) of the present embodiment can be synthesized by a coupling reaction with a halogenated aryl amine (see, for example, Non-Patent Literatures 5 and 6).

[Chem. 13]

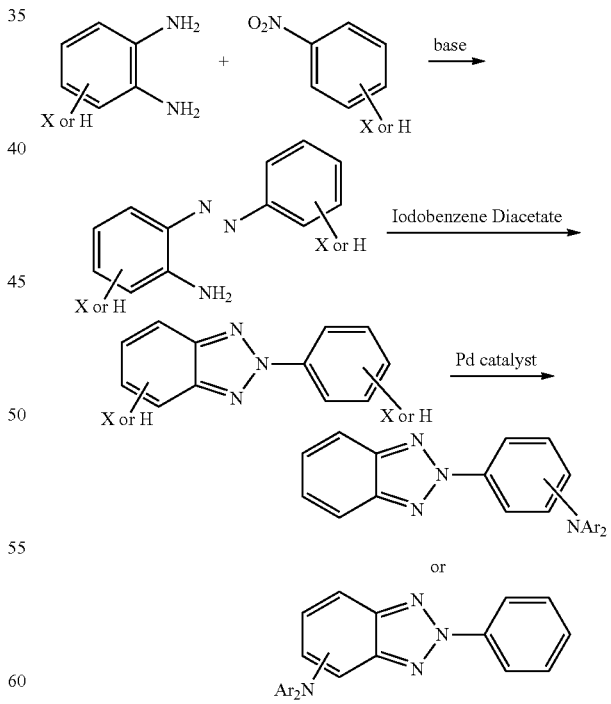

Specific examples of a preferable compound among benzazole compounds represented by the general formula (A-1), which are suitably used in the organic EL device of the present embodiment, are shown below, but the present invention is not limited to these compounds.

[Chem. 14]
(Compound 1)
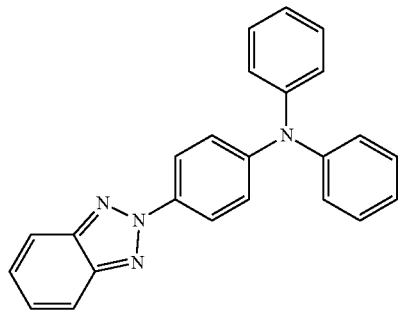
(Compound 2)
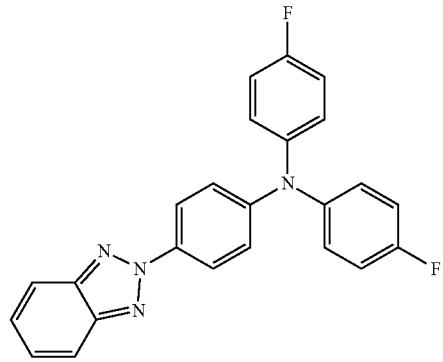
(Compound 3)
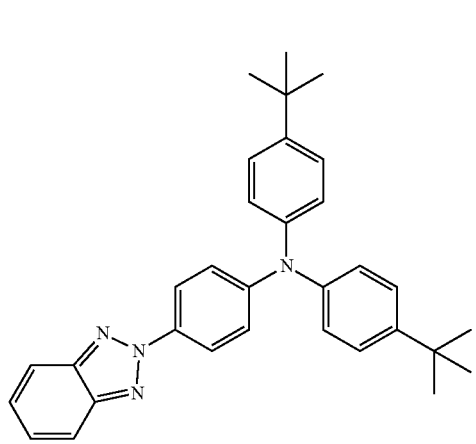
(Compound 4)
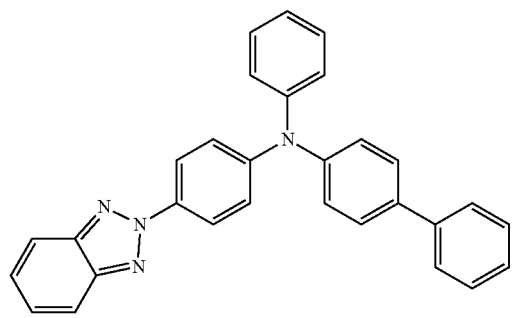
(Compound 5)
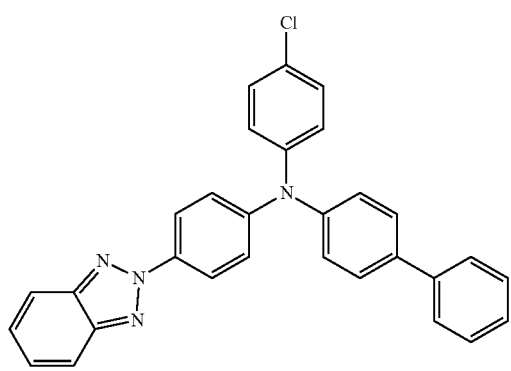
(Compound 6)
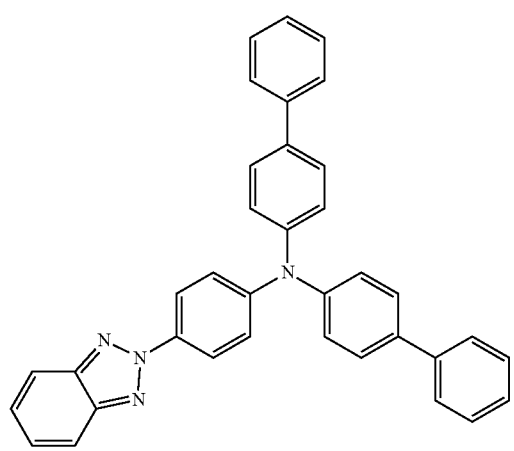

-continued
(Compound 7)
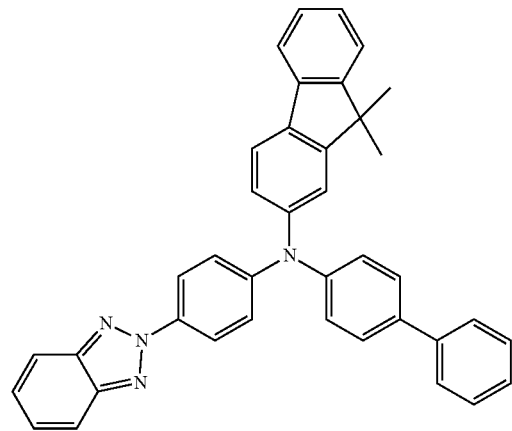
(Compound 8)
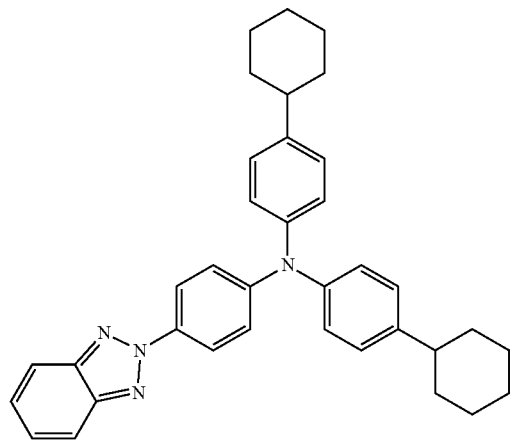
(Compound 9)
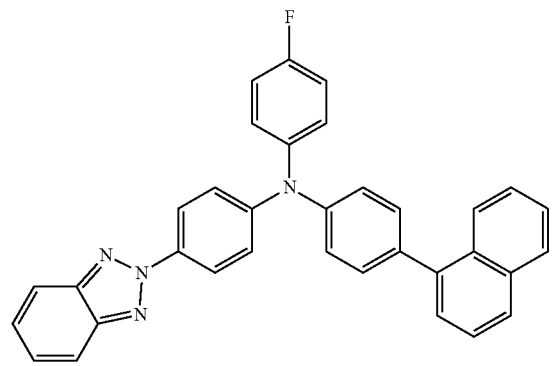
(Compound 10)
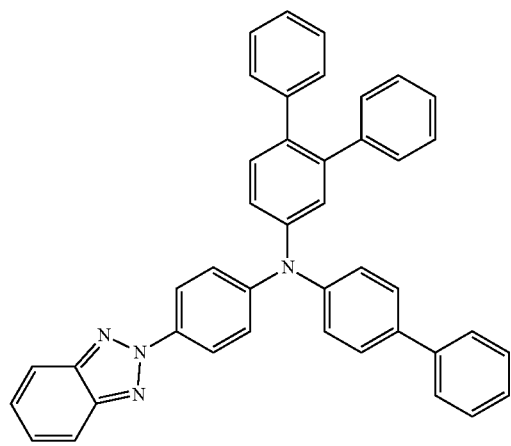
(Compound 11)
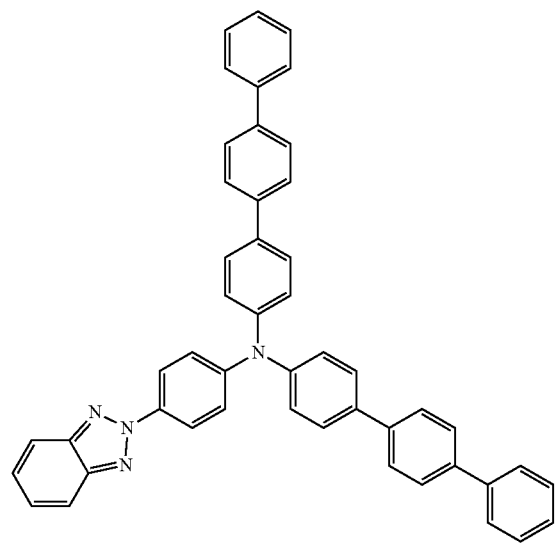
(Compound 12)
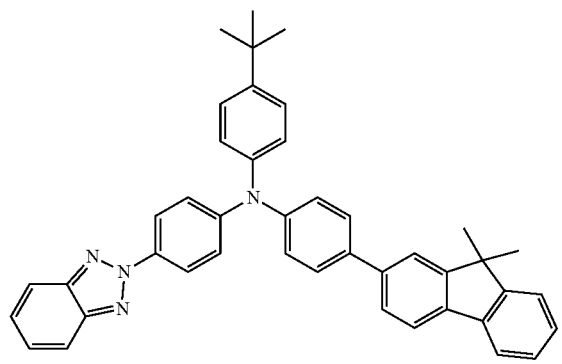

-continued
(Compound 13)
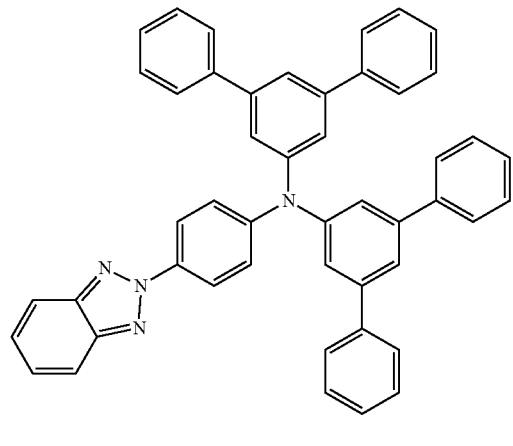
(Compound 14)
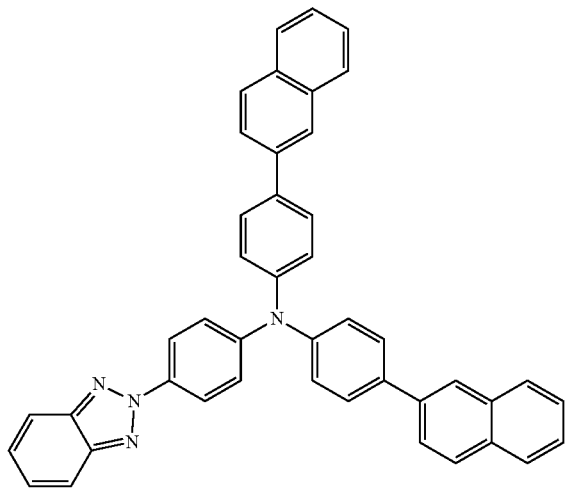
(Compound 15)
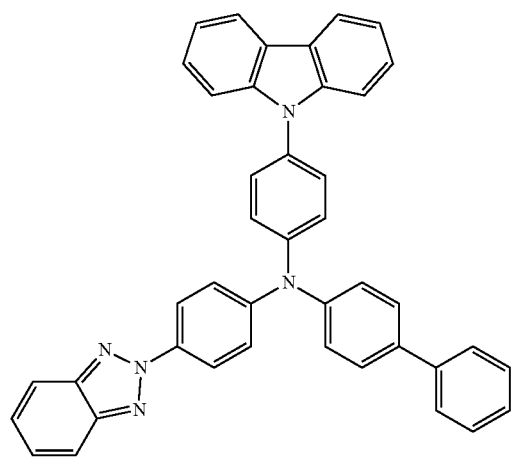
[Chem. 15]
(Compound 16)
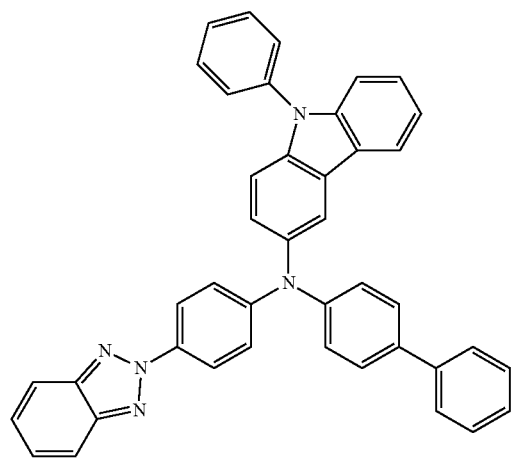
(Compound 17)
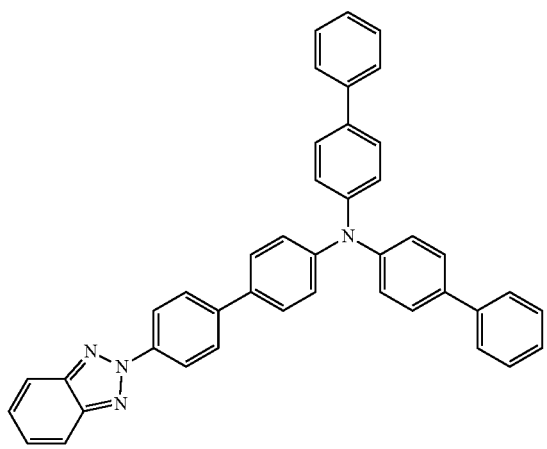

(Compound 18)
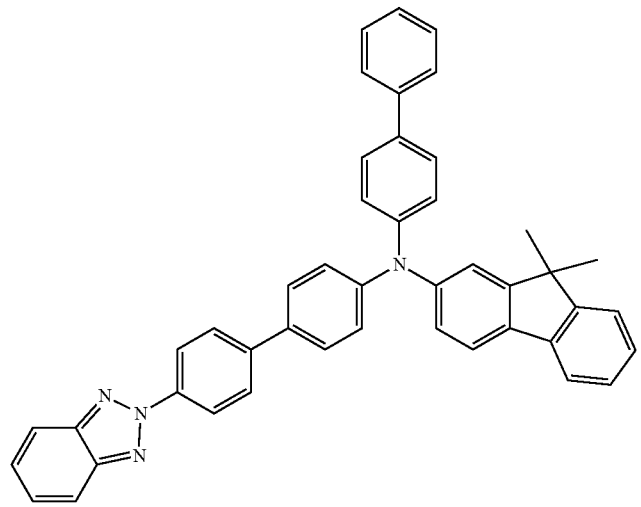
(Compound 19)
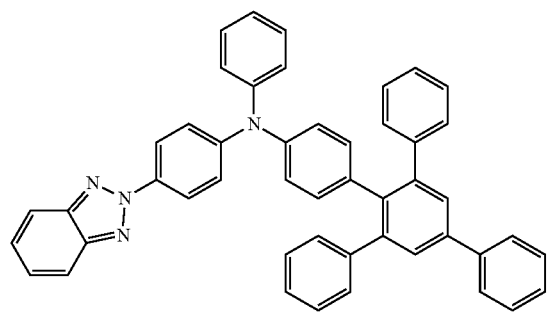
(Compound 20)
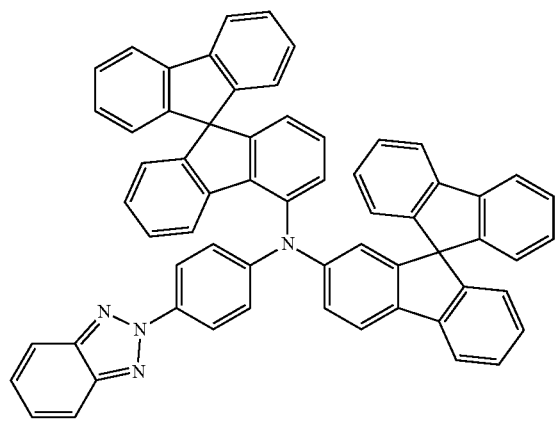
(Compound 21)
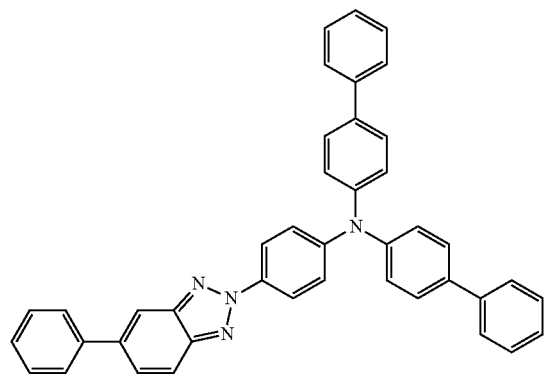
(Compound 22)
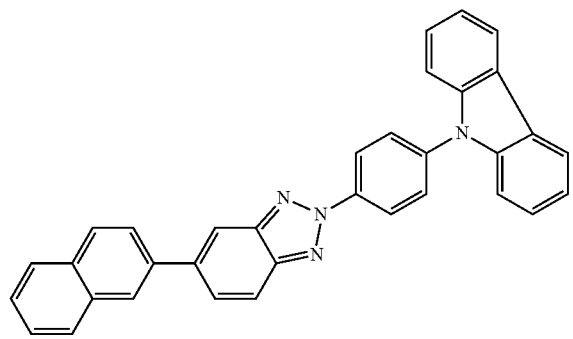

-continued
(Compound 23)
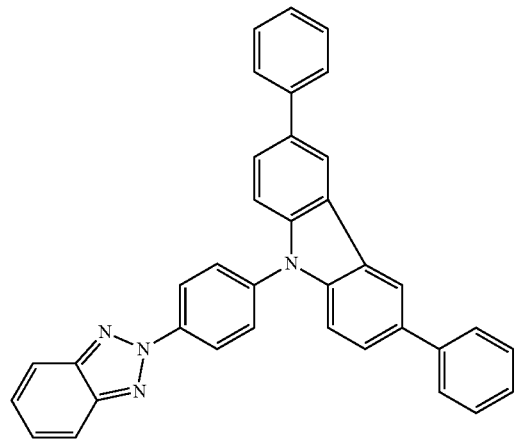
(Compound 24)
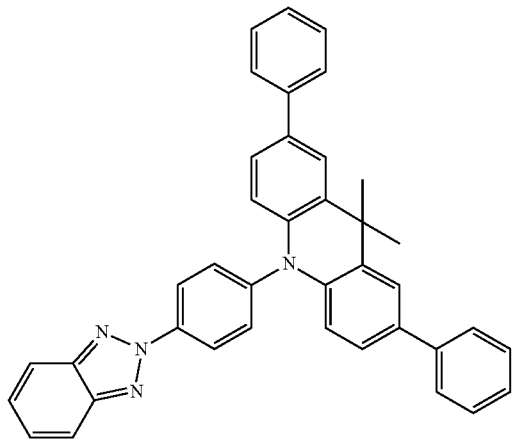
(Compound 25)
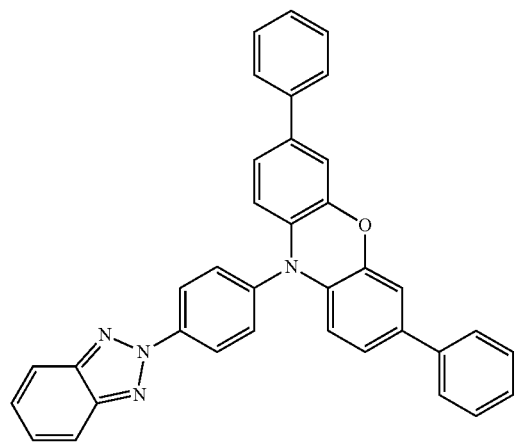
(Compound 26)
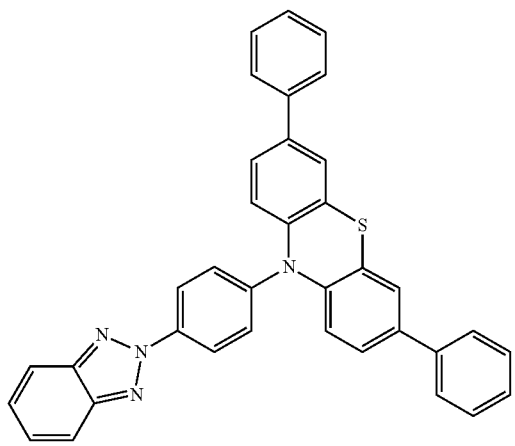
(Compound 27)
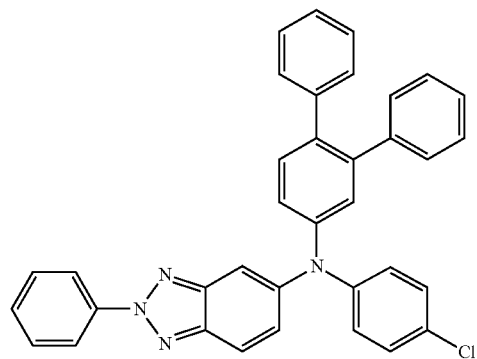
(Compound 28)
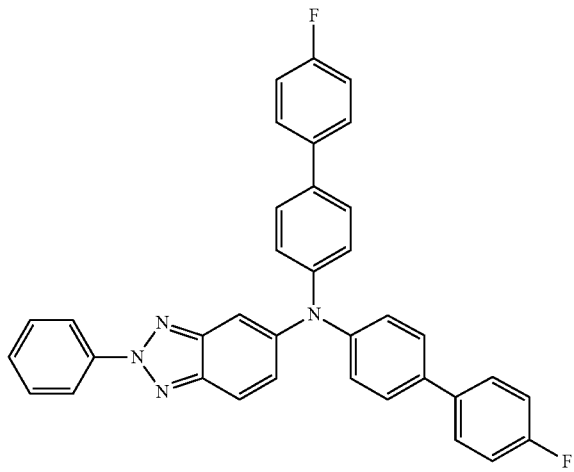

(Compound 29)
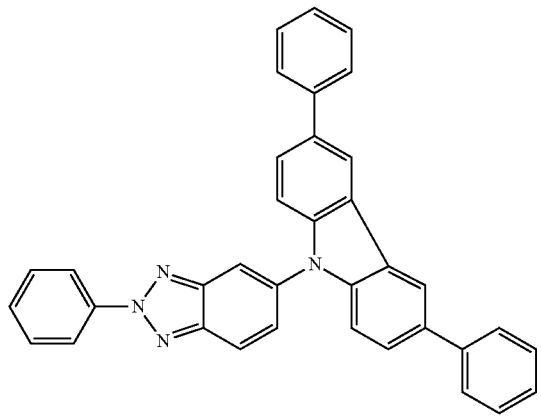
(Compound 30)
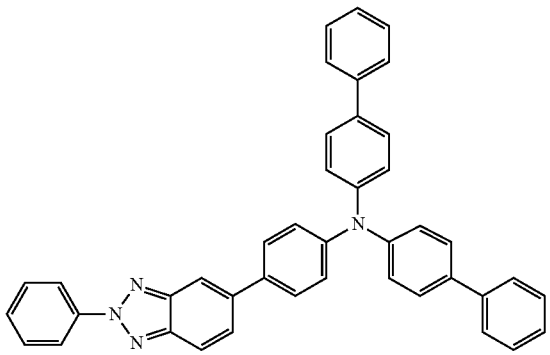
[Chem. 16]
(Compound 31)
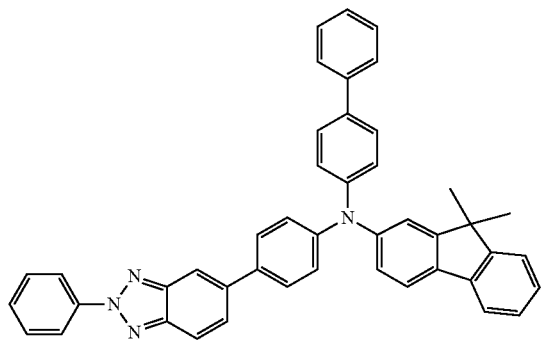
(Compound 32)
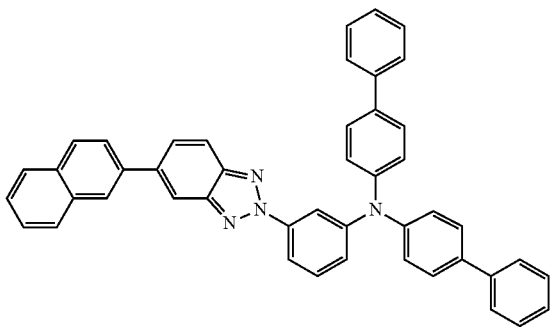
(Compound 33)
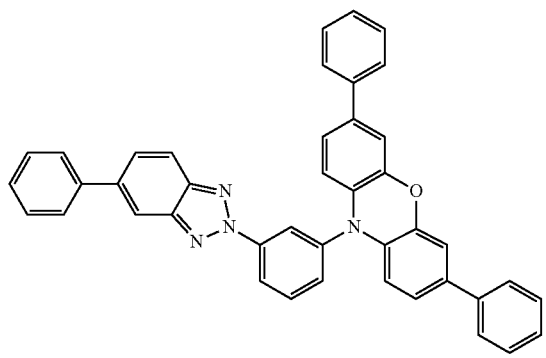
(Compound 34)
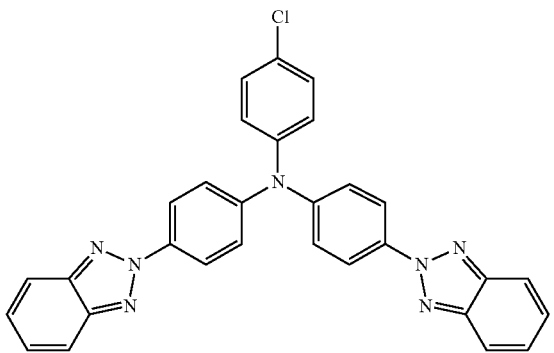
(Compound 35)
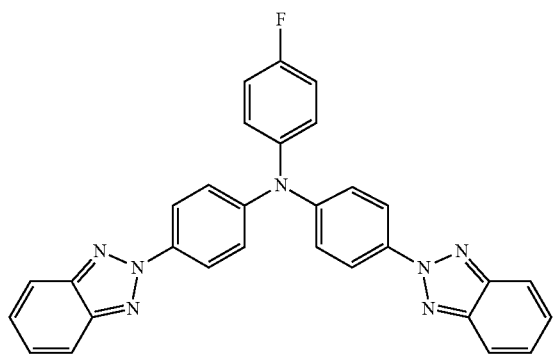
(Compound 36)
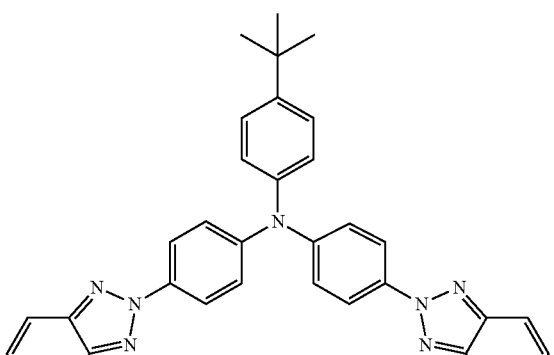

-continued
(Compound 37)
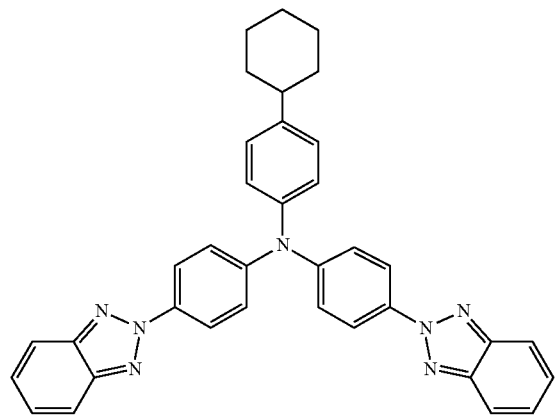
(Compound 38)
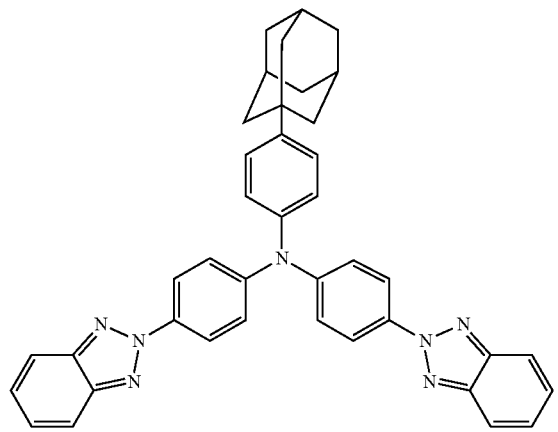
(Compound 39)
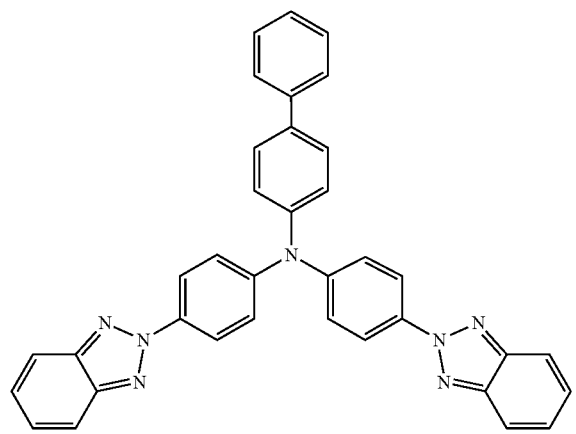
(Compound 40)
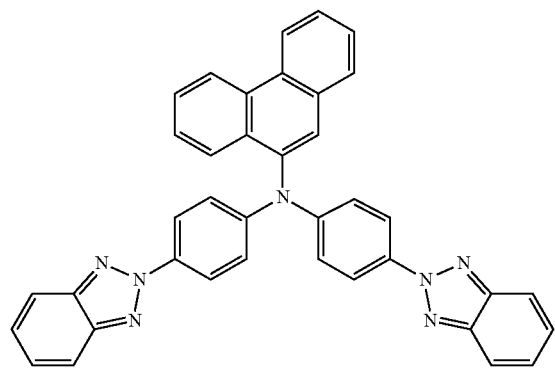
(Compound 41)
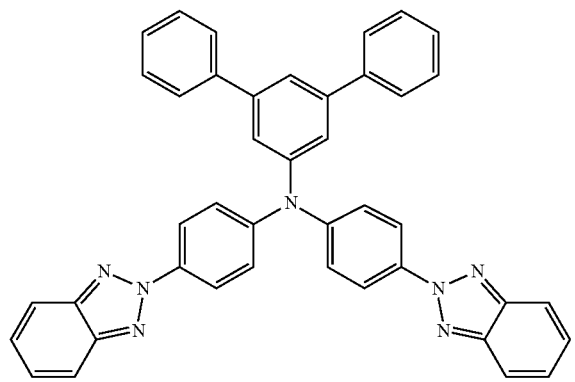

(Compound 42)
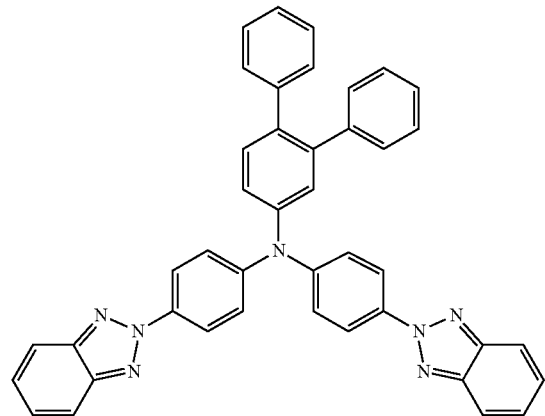
(Compound 43)
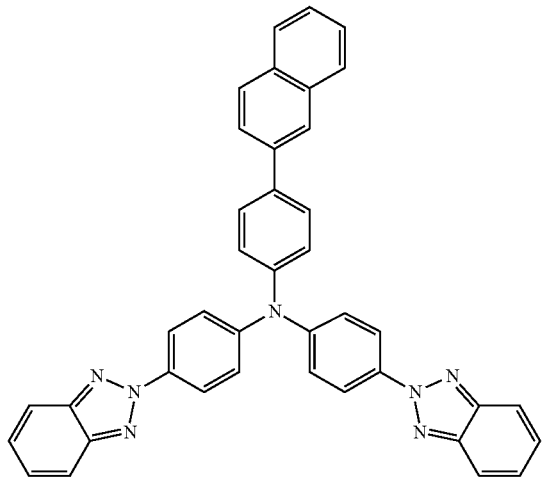
(Compound 44)
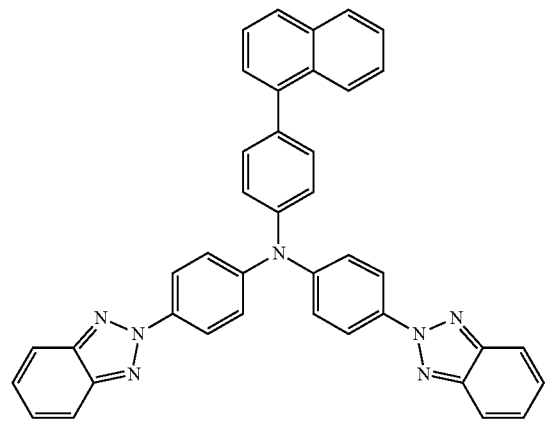
(Compound 45)
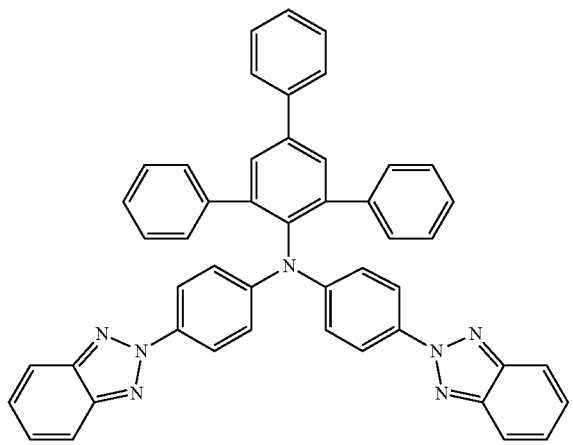
[Chem. 17]
(Compound 46)
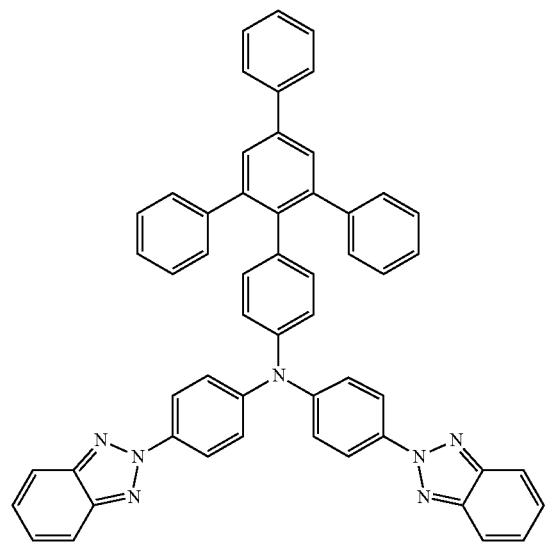
(Compound 47)
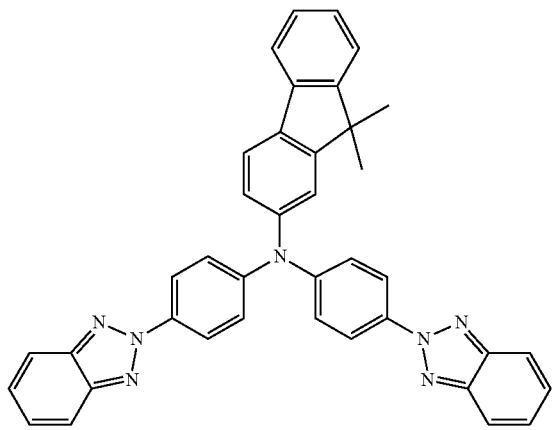

-continued
(Compound 48)
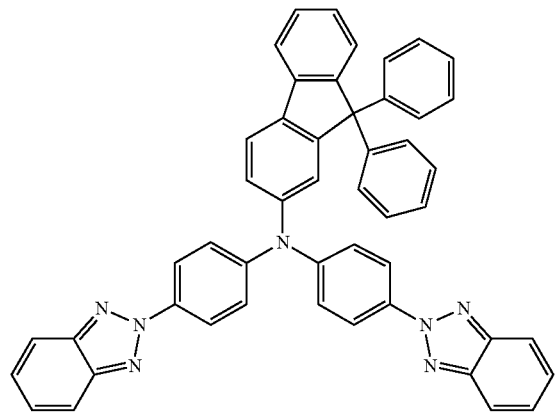
(Compound 49)
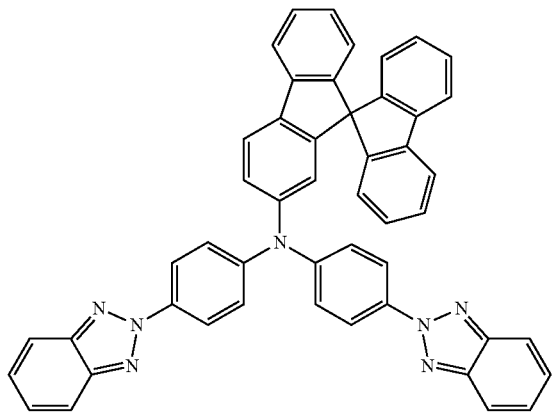
(Compound 50)
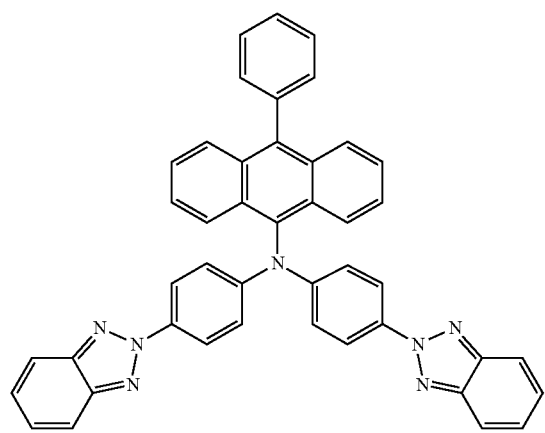
(Compound 51)
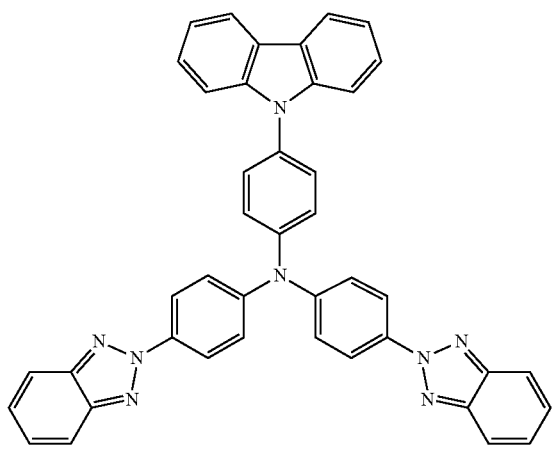
(Compound 52)
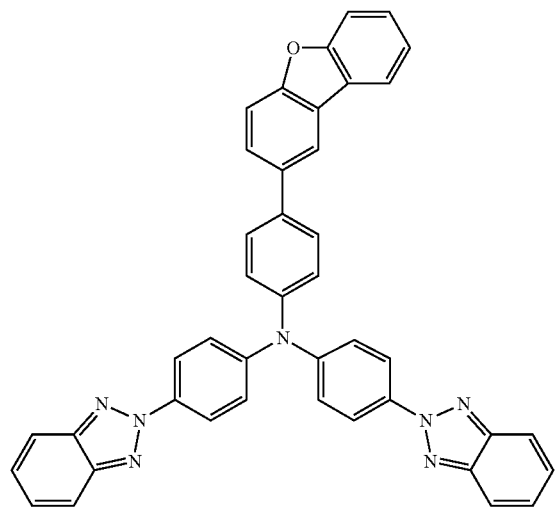
(Compound 53)
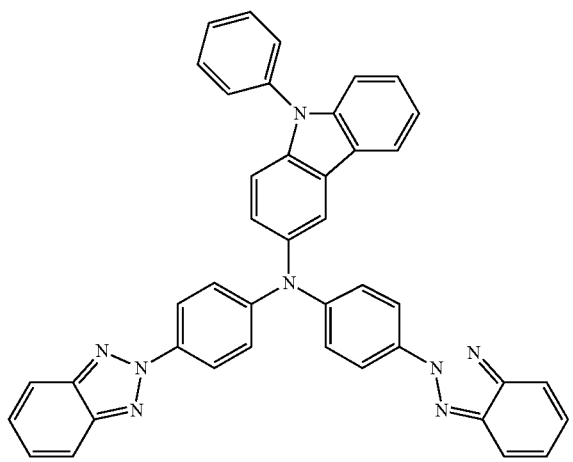

-continued
(Compound 54)
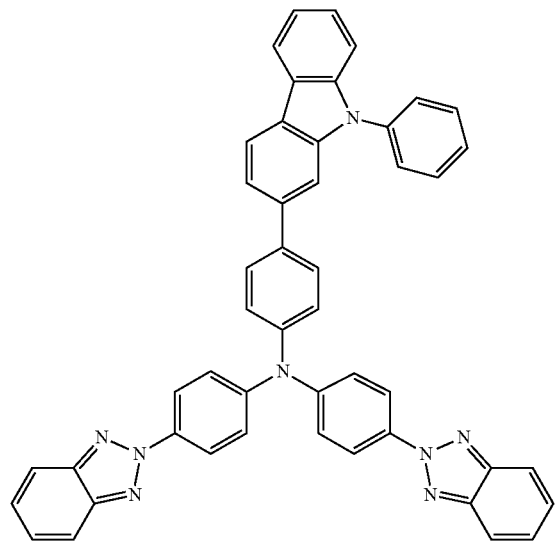
(Compound 55)
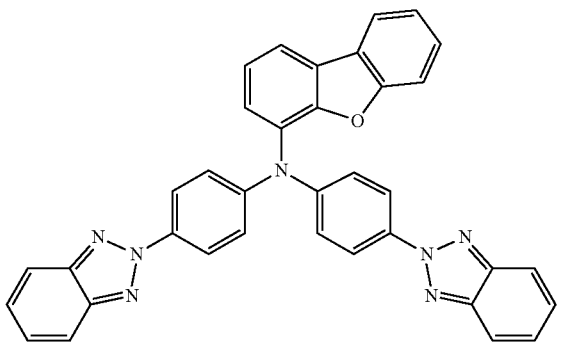
(Compound 56)
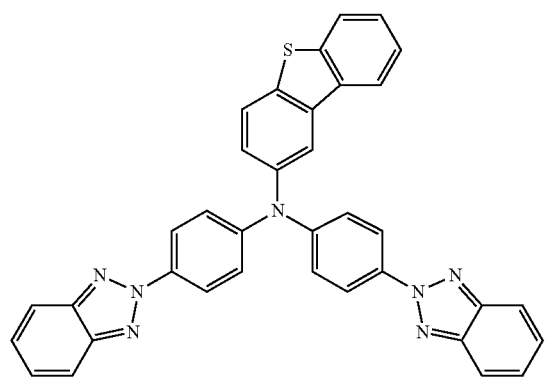
(Compound 57)
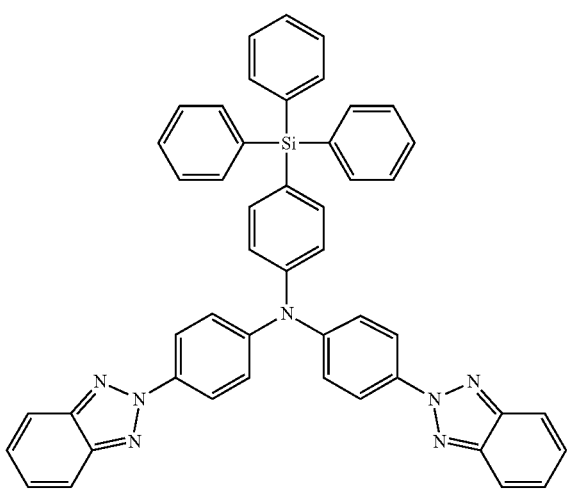
(Compound 58)
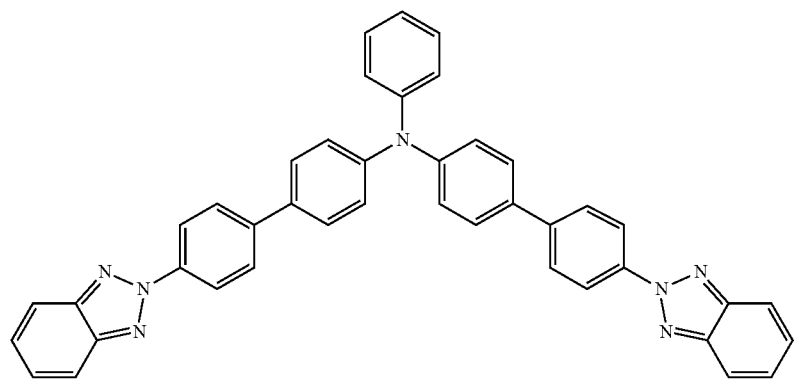

(Compound 59)
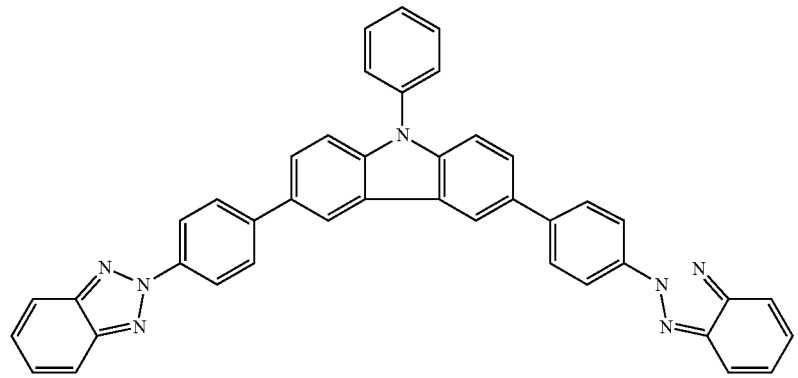
(Compound 60)
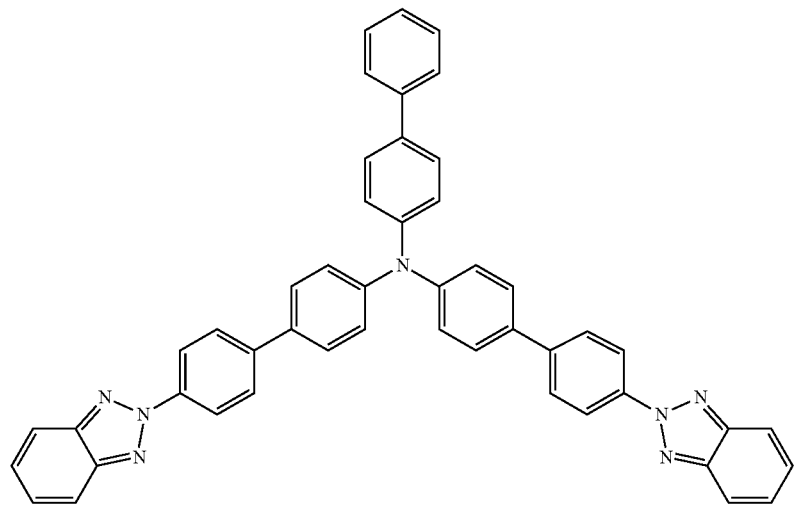
[Chem. 18]
(Compound 61) (Compound 62)
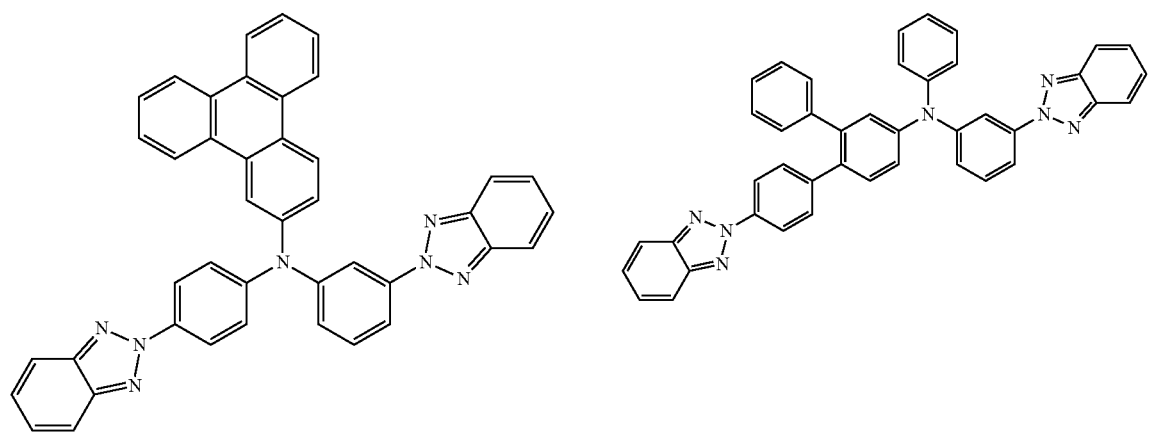

-continued
(Compound 63)
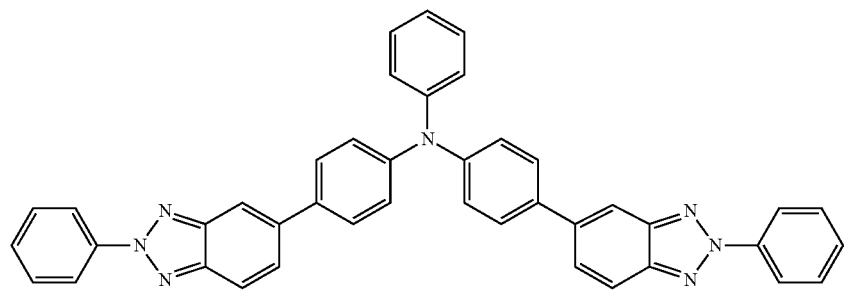
(Compound 64)
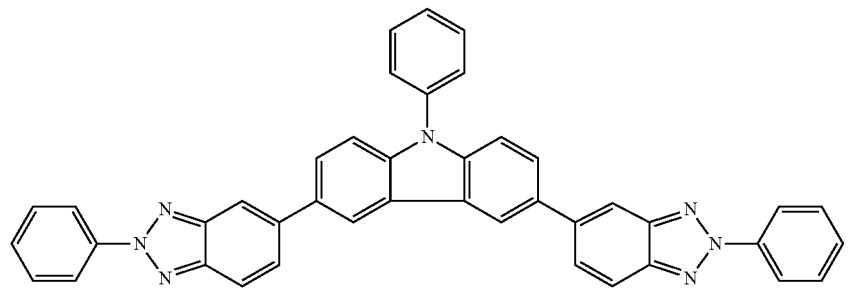
(Compound 65)
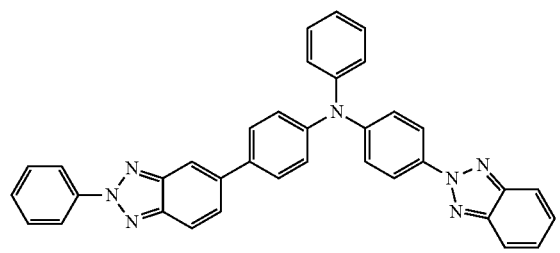
(Compound 66)
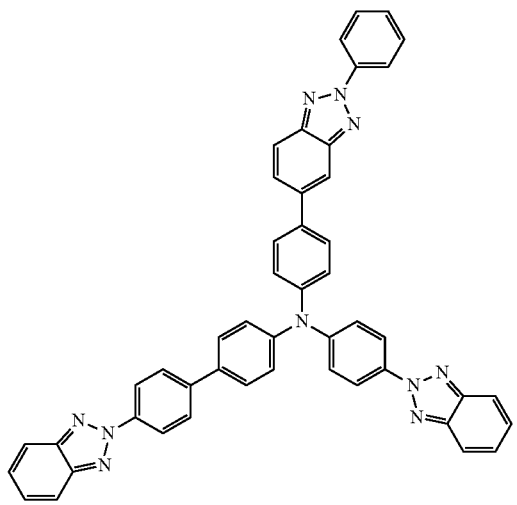
(Compound 67)
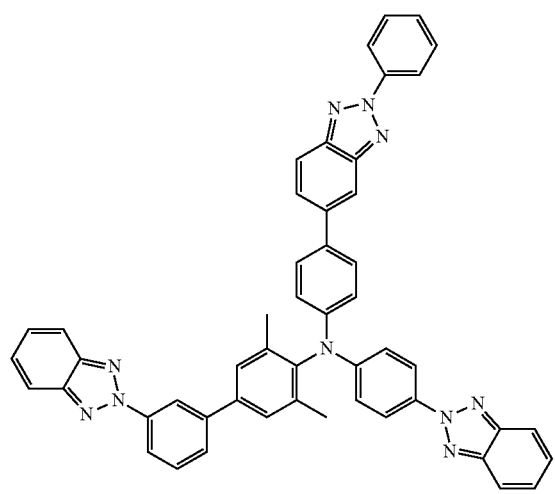
(Compound 68)
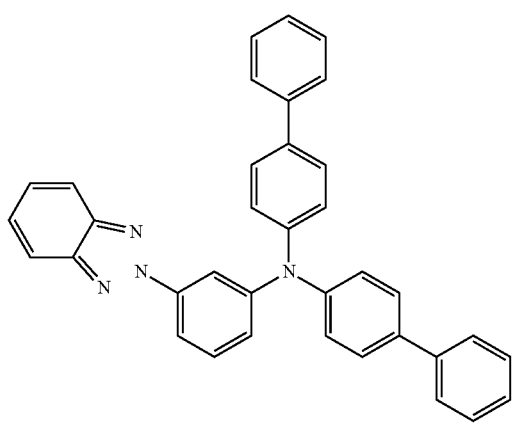

-continued
(Compound 69)
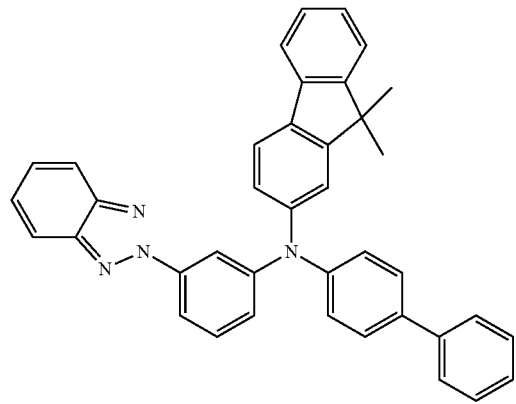
(Compound 70)
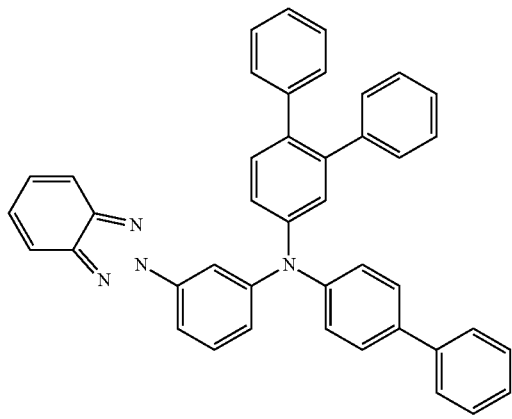
(Compound 71)
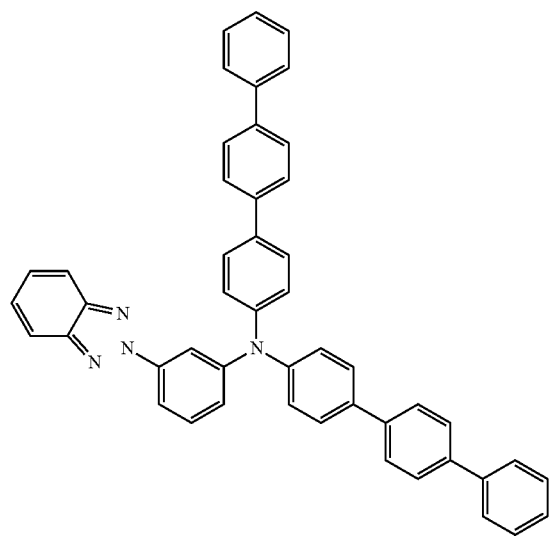
(Compound 72)
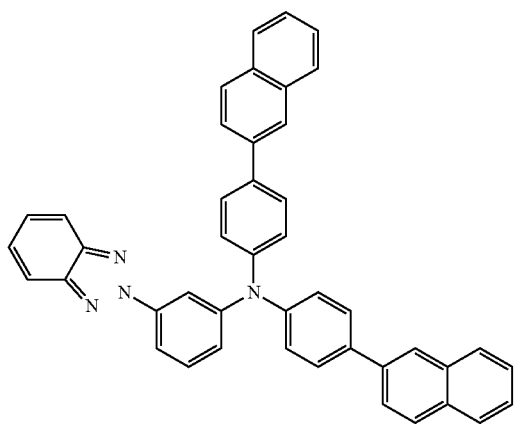
(Compound 73)
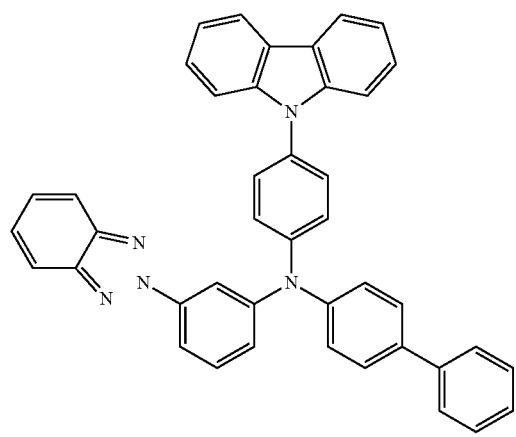
(Compound 74)
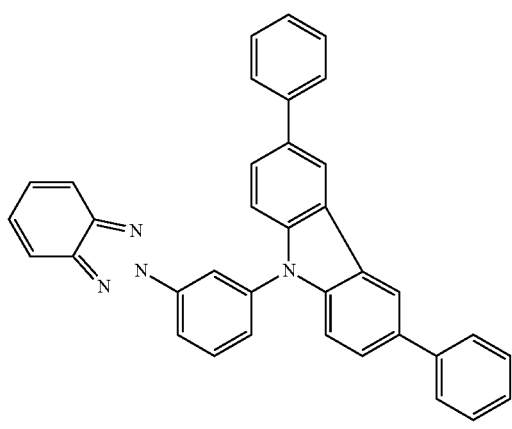

(Compound 75)
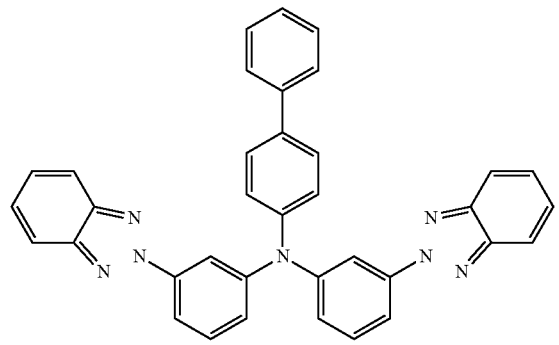
[Chem. 19]
(Compound 76)
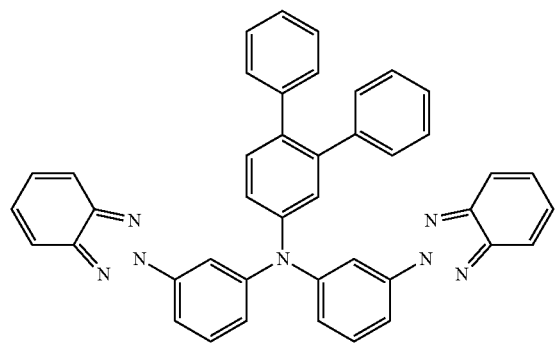
(Compound 77)
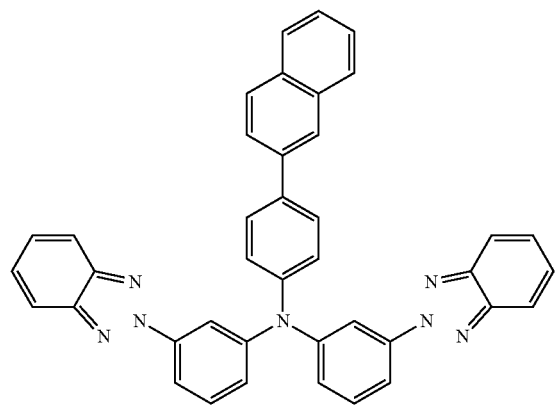
(Compound 78)
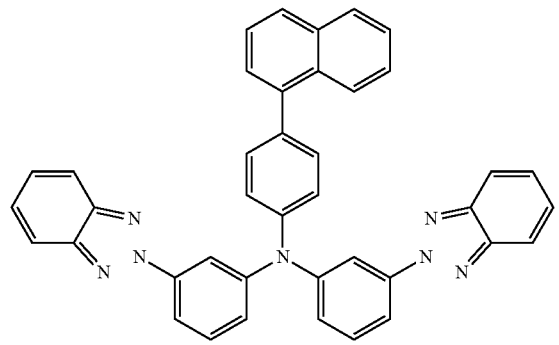
(Compound 79)
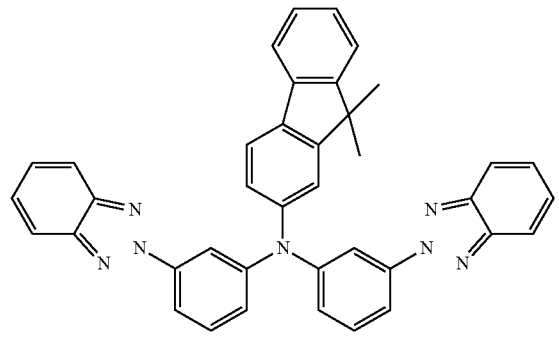
(Compound 80)
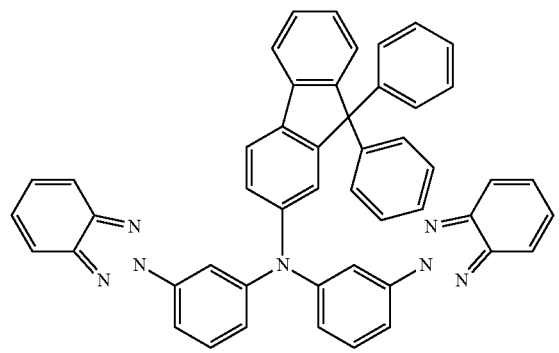
(Compound 81)
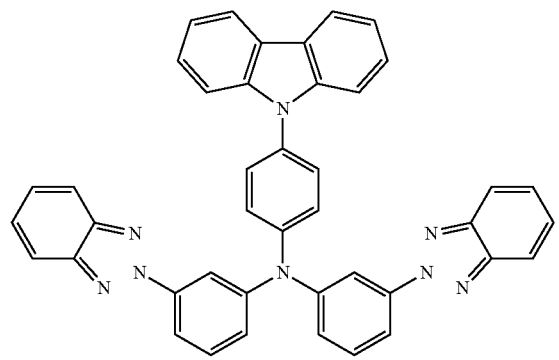

(Compound 82)

(Compound 83)

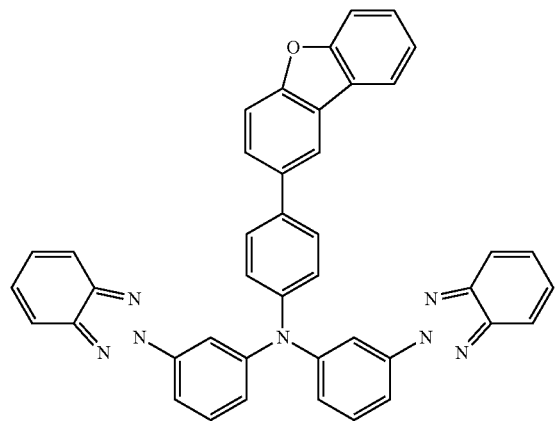

(Compound 84)

(Compound 85)

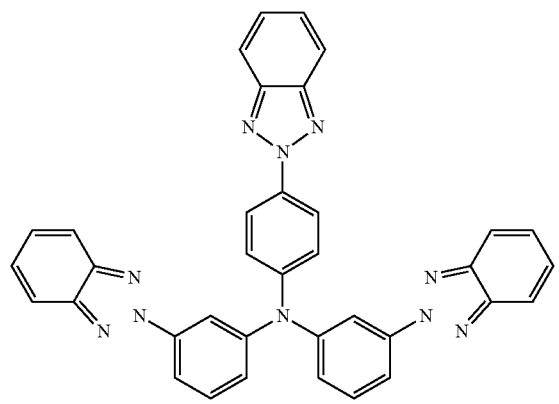

Purification of the compound represented by the general formula (A-1) is performed by purification by column chromatography, adsorption purification using silica gel, activated carbon, activated white clay or the like, recrystallization or crystallization using a solvent, sublimation purification, or the like. Identification of the compound is performed by NMR analysis. As physical property values, measurements of a melting point, a glass transition point (Tg) and a refractive index are performed in the following procedures. The melting point gives an index of deposition property, the glass transition point (Tg) gives an index of stability of a thin film, and the refractive index gives an index related to improvement in light extraction efficiency.

The melting point and the glass transition point (Tg) are measured with a high sensitivity differential scanning calorimeter (DSC 3100 SA manufactured by Bruker AXS GmbH) by using a powder of the compound represented by the general formula (A-1).

The refractive index and the extinction coefficient are measured by producing the thin film of the compound represented by the general formula (A-1) of 80 nm on a silicon substrate and using a spectroscopic measurement apparatus (F10-RT-UV manufactured by Filmetrics Japan, Inc.).

The absorbance is measured by using an ultraviolet-visible near-infrared spectrophotometer (V-650 manufactured by JASCO Corporation) by adjusting a toluene solution containing the compound represented by the general formula (A-1) to a concentration of $1.0 \times 10^{-5}$ mol/L. The absorption coefficient is calculated from a calibration curve obtained by adjusting a concentration of the toluene solution to four kinds of concentrations of $5.0 \times 10^{-6}$ mol/L, $1.0 \times 10^{-5}$ mol/L, $1.5 \times 10^{-5}$ mol/L, and $2.0 \times 10^{-5}$ mol/L, and measuring the absorbance at a peak wavelength with an ultraviolet-visible near-infrared spectrophotometer (V-650 manufactured by JASCO Corporation).

Examples of the structure of the organic EL device of the present embodiment include, in the case of a light emitting device having a top emission structure: a structure including an anode, a hole transport layer, a light emitting layer, an electron transport layer, a cathode, and a capping layer in this order on a glass substrate; a structure further including a hole injection layer between the anode and the hole transport layer; a structure further including an electron blocking layer between the hole transport layer and the light emitting layer; a structure further including a hole blocking layer between the light emitting layer and the electron transport layer; and a structure further including an electron injection layer between the electron transport layer and the cathode. In these multilayer structures, some of organic layers can be omitted or combined, and examples thereof can include: a configuration in which the hole injection layer and the hole transport layer are combined; a configuration in which the hole transport layer and the electron blocking layer are combined; a configuration in which the hole blocking layer and the electron transport layer are combined; a configuration in which the electron transport layer and the electron injection layer are combined, and the like. A configuration in which two or more organic layers having the same function are laminated can be also used, which can include a configuration in which two hole transport layers are laminated; a configuration in which two light emitting layers are laminated; a configuration in which two electron transport layers are laminated; a configuration in which two capping layers are laminated, or the like.

A total thickness of layers of the organic EL device is preferably about 200 nm to 750 nm and more preferably about 350 nm to 600 nm. A thickness of the capping layer is preferably 30 nm to 120 nm and more preferably 40 nm to 80 nm. In this case, good light extraction efficiency can be obtained. The thickness of the capping layer can be appropriately changed in accordance with the type of the light emitting material used for the light emitting device, the thickness of the organic EL device other than the capping layer, and the like.

As an anode of the organic EL device of the present embodiment, an electrode material having a large work function, such as ITO or gold is used.

As the hole injection layer of the organic EL device of the present embodiment, use can be made of an aryl amine compound having a structure in which three or more triphenyl amine structures are linked by a single bond or a divalent group containing no hetero atom in the molecule, such as star burst type triphenyl amine derivatives, a material such as various triphenyl amine tetramers, a porphyrin compound represented by copper phthalocyanine, and a heterocyclic compound having acceptor properties such as hexacyano azatriphenylene, a coating type polymer material, and the like. These may be used to form a film alone or may be used as a single layer formed by being mixed with another material, or may be used in a laminated structure of layers each formed by alone, layers each formed by being mixed, or a layer formed by alone and a layer formed by being mixed. These materials can form a thin film by a publicly known method such as a spin coating method or an ink jet method in addition to a deposition method.

As the hole transport layer of the organic EL device of the present embodiment, use can be made preferably of benzidine derivatives such as N,N'-diphenyl-N,N'-di(m-tolyl) benzidine (hereinafter abbreviated as TPD), N,N'-diphenyl-N,N'-di(α-naphthyl) benzidine (hereinafter referred to as NPD) and N,N,N',N'-tetrabiphenylyl benzidine, 1,1-bis[4-(di-4-tolyl amino) phenyl] cyclohexane (hereinafter abbreviated as TAPC), in particular, aryl amine compound having a structure in which two triphenyl amine structures are linked by a single bond or a divalent group containing no hetero atom in the molecule, such as, N,N,N',N'-tetrabiphenylyl benzidine, and the like. In addition, it is preferable to use an aryl amine compound having a structure in which three or more triphenyl amine structures are linked with a single bond or a divalent group containing no hetero atom in the molecule, such as various kinds of triphenyl amine trimer and tetramer, and the like. These may be used to form a film alone or may be used as a single layer formed by being mixed with another material, or may be used in a laminated structure of layers each formed by alone, layers each formed by being mixed, or a layer formed by alone and a layer formed by being mixed. As a hole injection and transport layer, a coating type polymer material such as poly(3,4-ethylene dioxythiophene) (hereinafter abbreviated as PEDOT)/poly(styrene sulfonate) (hereinafter abbreviated as PSS) can be used. These materials can form a thin film by a publicly known method such as a spin coating method or an ink jet method in addition to a deposition method.

In addition, in the hole injection layer or the hole transport layer, a material that is generally used for these layers and is further P-doped with trisbromo phenyl amine hexachloro antimony, a radialene derivative (see, for example, Patent Literature 3), or the like, and a polymer compound having a structure of a benzidine derivative such as TPD in a partial structure thereof can be used.

As the electron blocking layer of the organic EL device of the present embodiment, use can be made of a compound having an electron blocking action, such as carbazole derivatives such as 4,4',4''-tri(N-carbazolyl) triphenyl amine (hereinafter referred to as TCTA), 9,9-bis[4-(carbazole-9-yl) phenyl] fluorene, 1,3-bis(carbazole-9-yl) benzene (hereinafter abbreviated as mCP), and 2,2-bis(4-carbazole-9-yl-phenyl) adamantane (hereinafter abbreviated as Ad-Cz), and compounds having a triphenyl silyl group and a triaryl amine structure represented by 9-[4-(carbazole-9-yl) phenyl]-9-[4-(triphenyl silyl) phenyl]-9H-fluorene. These may be used to form a film alone or may be used as a single layer formed by being mixed with another material, or may be used in a laminated structure of layers each formed by alone, layers each formed by being mixed, or a layer formed by alone and a layer formed by being mixed. These materials can form a thin film by a publicly known method such as a spin coating method or an ink jet method in addition to a deposition method.

As the light emitting layer of the organic EL device of the present embodiment, use can be made of, in addition to the metal complexes of quinolinol derivatives as typified by $Alq_3$, various metal complexes, anthracene derivatives, bisstyryl benzene derivatives, pyrene derivatives, oxazole derivatives, poly para-phenylene vinylene derivatives, and the like. The light emitting layer may be constituted by a host material and a dopant material. As the host material, the anthracene derivatives are preferably used, and in addition to the above-described light emitting materials, heterocyclic compounds having an indole ring as a partial structure of a condensed ring, heterocyclic compounds having an carbazole ring as a partial structure of a condensed ring, carbazole derivatives, thiazole derivatives, benzimidazole derivatives, polydialkyl fluorene derivatives, and the like can be used. As the dopant material, quinacridone, coumarin, rubrene, perylene and derivatives thereof, benzopyran derivatives, rhodamine derivatives, amino styryl derivatives, and the like can be used. These may be used to form a film alone or may be used as a single layer formed by being mixed with another material, or may be used in a laminated structure of layers each formed by alone, layers each formed by being mixed, or a layer formed by alone and a layer formed by being mixed.

A phosphorescence emitter can also be used as the light emitting material. As the phosphorescence emitter, a phosphorescence emitter of a metal complex of iridium, platinum, or the like can be used. Green phosphorescence emitters such as $Ir(ppy)_3$, blue phosphorescence emitters such as FIrpic and FIr6, red phosphorescence emitters such as $Btp_2Ir(acac)$, and the like can be used, and as the host material at this time, carbazole derivatives such as 4,4'-di (N-carbazolyl) biphenyl (hereinafter abbreviated as CBP), TCTA and mCP can be used as the host material having hole injection and transport properties. As the electron transport host material, p-bis(triphenyl silyl) benzene (hereinafter abbreviated as UGH2), 2,2',2"-(1,3,5-phenylene)-tris(1-phenyl-1H-benzimidazole) (hereinafter abbreviated as TPBI) and the like can be used, and an organic EL device having a high performance can be produced.

In order to avoid concentration quenching, doping of the phosphorescent emitting material into the host material is preferably performed by co-deposition in a range of 1 to 30 weight percents with respect to the entire light emitting layer.

It is also possible to use materials that emit delayed fluorescence, such as PIC-TRZ, CC2TA, PXZ-TRZ, and CDCB derivatives such as 4CzIPN as the light emitting material. (See, for example, Non-Patent Literature 7.) These materials can form a thin film by a publicly known method such as a spin coating method or an ink jet method in addition to a deposition method.

As the hole blocking layer of the organic EL device of the present embodiment, use can be made of compounds having a hole blocking effect, such as phenanthroline derivatives such as bathocuproine (hereinafter abbreviated as BCP), metal complexes of quinolinol derivatives such as aluminum (III) bis(2-methyl-8-quinolinate)-4-phenyl phenolate (hereinafter abbreviated as BAlq), various rare earth complexes, triazole derivatives, triazine derivatives, pyrimidine derivatives, oxadiazole derivatives, benzazole derivatives, and the like. These materials may also double as materials of the electron transport layer. These may be used to form a film alone or may be used as a single layer formed by being mixed with another material, or may be used in a laminated structure of layers each formed by alone, layers each formed by being mixed, or a layer formed by alone and a layer formed by being mixed. These materials can form a thin film by a publicly known method such as a spin coating method or an ink jet method in addition to a deposition method.

As the electron transport layer of the organic EL device of the present embodiment, use can be made of, in addition to metal complexes of quinolinol derivatives as typified by Alq$_3$ and BAlq, various metal complexes, triazole derivatives, triazine derivatives, pyrimidine derivatives, oxadiazole derivatives, pyridine derivatives, benzimidazole derivatives, benzazole derivatives, thiadiazole derivatives, anthracene derivatives, carbodiimide derivatives, quinoxaline derivatives, pyridindole derivatives, phenanthroline derivatives, silole derivatives, and the like. These may be used to form a film alone or may be used as a single layer formed by being mixed with another material, or may be used as a laminated structure of layers each formed by alone, layers each formed by being mixed, or a layer formed by alone and a layer formed by being mixed. These materials can form a thin film by a publicly known method such as a spin coating method or an ink jet method in addition to a deposition method.

As the electron injection layer of the organic EL device of the present embodiment, use can be made of alkali metal salts such as lithium fluoride and cesium fluoride, alkaline earth metal salts such as magnesium fluoride, metal complexes of quinolinol derivatives such as lithium quinolinol, metal oxides such as aluminum oxide, metals such as ytterbium (Yb), samarium (Sm), calcium (Ca), strontium (Sr), and cesium (Cs), and the like, but this can be omitted in preferred selection of the electron transport layer and the cathode.

Further, in the electron injection layer or the electron transport layer, it is possible to use a material that is generally used for these layers and is further N-doped with a metal such as cesium.

As the cathode of the organic EL device of the present embodiment, an electrode material having a low work function such as aluminum, an alloy having a lower work function such as a magnesium silver alloy, a magnesium calcium alloy, a magnesium indium alloy, or an aluminum magnesium alloy, ITO, IZO, and the like can be used as an electrode material.

As the capping layer of the organic EL device of the present embodiment, an amine compound having a benzazole ring structure represented by the general formula (A-1) or the like is preferably used. These may be used to form a film alone or may be used as a single layer formed by being mixed with another material, or may be used as a laminated structure of layers each formed by alone, layers each formed by being mixed, or a layer formed by alone and a layer formed by being mixed. These materials can form a thin film by a publicly known method such as a spin coating method or an ink jet method in addition to a deposition method.

Although the organic EL device having a top emission structure has been described above, the present invention is not limited thereto, and the organic EL device having a bottom emission structure and an organic EL device having a dual emission structure that emits light from both the top and bottom can be similarly applied. In these cases, an electrode in a direction in which light is extracted from the light emitting device to the outside is required to be transparent or translucent.

The refractive index of the material constituting the capping layer is preferably larger than a refractive index of the adjacent electrode. That is, although light extraction efficiency in the organic EL device is improved by the capping layer, the effect thereof is effective in the case where the reflectance at an interface between the capping layer and the material in contact with the capping layer is greater since an effect of optical interference is great. Therefore, the refractive index of the material constituting the capping layer is preferably larger than the refractive index of the adjacent electrode, and the refractive index may be 1.70 or more, more preferably 1.80 or more, and particularly preferably 1.85 or more.

The embodiments of the present invention will be described more specifically by Examples below, but the present invention is by no means restricted to the following Examples so long as it does not exceed the gist thereof.

Example 1

Synthesis of {4'-(benzotriazole-2-yl) biphenyl-4-yl}-bis-(biphenyl-4-yl)-amine (Compound 17)

Into a nitrogen substituted reaction vessel, 2-(4-bromophenyl)-2H-benzotriazole: 3.7 g, bis-(biphenyl-4-yl)-{4-(4,4,5,5-tetramethyl-[1,3,2] dioxaborane-2-yl)-phenyl}-amine: 9.4 g, toluene: 80 mL, and ethanol: 20 mL were added, then an aqueous solution where potassium carbonate: 5.6 g was dissolved in H₂O: 20 mL in advance was added, and nitrogen gas was aerated while the solution was irradiated with ultrasonic waves for 30 minutes. Tetrakistriphenyl phosphine palladium: 0.8 g was added and stirred under heated reflux for 4 hours. After standing to cool, H₂O was added, an organic layer was extracted by a liquid separation operation and concentrated under reduced pressure to obtain a crude product. The obtained crude product was purified by column chromatography (carrier: silica gel, eluent: toluene/n-hexane) to obtain yellow powder of {4'-(benzotriazole-2-yl) biphenyl-4-yl}-bis-(biphenyl-4-yl)-amine (compound 17): 6.4 g (yield: 85%).

[Chem. 20]

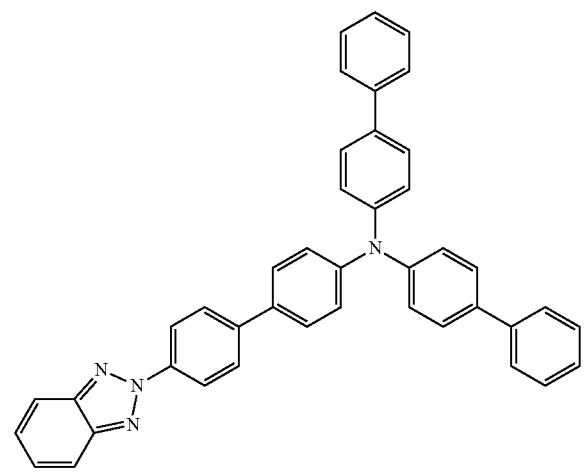

(Compound 17)

A structure of the obtained yellow powder was identified with NMR.

The following 30 hydrogen signals were detected with ¹H-NMR (THF-d₈). δ (ppm)=8.46 (2H), 7.94 to 7.92 (2H), 7.88 (2H), 7.69 (2H), 7.62 (4H), 7.59 (4H), 7.43 to 7.38 (6H), 7.29 to 7.23 (8H).

Example 2

Synthesis of {4-(benzotriazole-2-yl) phenyl}-bis (biphenyl-4-yl)-amine (Compound 6)

Into a reaction vessel, 2-(4-bromophenyl)-2H-benzotriazole: 9.0 g, bis-(biphenyl-4-yl)-amine: 9.6 g, t-butoxy sodium: 4.3 g, and toluene: 150 mL were added, and nitrogen gas was aerated while the solution was irradiated with ultrasonic waves for 30 minutes. Palladium (II) acetate: 0.1 g and a 50% (w/v) toluene solution of tri-(t-butyl) phosphine: 0.24 mL were added and stirred under heated reflux for 2 hours. After standing to cool, toluene was added to perform dispersion washing, insoluble matter was filtered off, and silica gel and active white clay were added to the filtrate to perform adsorption purification. Adsorbent was removed by filtration and the filtrate was concentrated to obtain a crude product. The crude product was purified by crystallization with a toluene/acetone mixed solvent to collect a precipitated solid, to obtain yellow powder of {4-(benzotriazole-2-yl) phenyl}-bis(biphenyl-4-yl)-amine (compound 6): 11.6 g (yield: 75.3%).

[Chem.21]

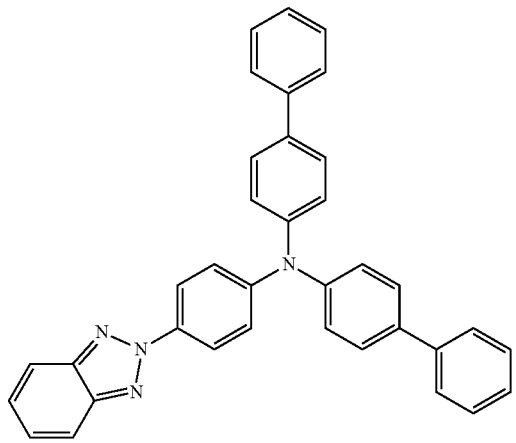

(Compound 6)

A structure of the obtained yellow powder was identified with NMR.

The following 26 hydrogen signals were detected with ¹H-NMR (CDCl₃). δ (ppm)=8.27 to 8.31 (2H), 7.95 to 7.99 (2H), 7.58 to 7.66 (8H), 7.28 to 7.51 (14H).

Example 3

Synthesis of {4-(benzotriazole-2-yl) phenyl}-(biphenyl-4-yl)-9,9-dimethyl-9H-fluorene-2-yl)-amine (Compound 7)

Into a reaction vessel, 2-(4-bromophenyl)-2H-benzotriazole: 8.3 g, (biphenyl-4-yl)-(9,9-dimethyl-9H-fluorene-2-yl)-amine: 10.0 g, t-butoxy sodium: 4.0 g, and toluene: 150 mL were added, and nitrogen gas was aerated while the solution was irradiated with ultrasonic waves for 30 minutes. Palladium (II) acetate: 0.1 g and a 50% (w/v) toluene solution of tri-(t-butyl) phosphine: 0.22 mL were added and stirred under heated reflux for 2 hours. After standing to cool, toluene was added to perform dispersion washing, insoluble matter was filtered off, and silica gel and active white clay were added to the filtrate to perform adsorption purification. Adsorbent was removed by filtration and the filtrate was concentrated to obtain a crude product. The crude product was purified by crystallization with acetone to collect a precipitated solid, to obtain yellow powder of {4-(benzotriazole-2-yl) phenyl}-(biphenyl-4-yl)-(9,9-dimethyl-9H-fluorene-2-yl)-amine (compound 7): 12.3 g (yield: 80.4%).

[Chem. 22]

(Compound 7)

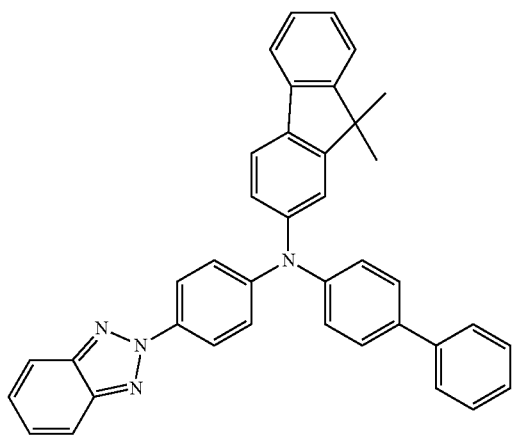

A structure of the obtained yellow powder was identified with NMR.

The following 30 hydrogen signals were detected with $^1$H-NMR (CDCl$_3$). δ (ppm)=8.24 to 8.27 (2H), 7.94 to 7.97 (2H), 7.57 to 7.72 (6H), 7.28 to 7.50 (13H), 7.16 to 7.20 (1H), 1.48 (6H).

Example 4

Synthesis of 9-{4-(benzotriazole-2-yl) phenyl}-3,6-diphenyl-9H-carbazole (Compound 23)

Into a reaction vessel, 2-(4-bromophenyl)-2H-benzotriazole: 7.6 g, 3,6-biphenyl-9H-carbazole: 8.0 g, t-butoxy sodium: 3.6 g, and toluene: 130 mL were added, and nitrogen gas was aerated while the solution was irradiated with ultrasonic waves for 30 minutes. Palladium (II) acetate: 0.1 g and a 50% (w/v) toluene solution of tri-(t-butyl) phosphine: 0.20 mL were added and stirred under heated reflux for 12 hours. After standing to cool, toluene was added to perform dispersion washing, insoluble matter was filtered off, and silica gel and active white clay were added to the filtrate to perform adsorption purification. Adsorbent was removed by filtration and the filtrate was concentrated to obtain a crude product. The crude product was purified by crystallization with acetone to collect a precipitated solid, to obtain yellow powder of 9-{4-(benzotriazole-2-yl) phenyl}-3,6-diphenyl-9H-carbazole (compound 23): 6.9 g (yield: 54%).

[Chem. 23]

(Compound 23)

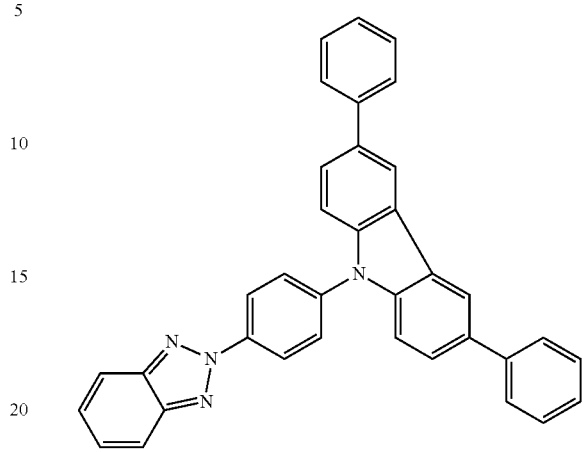

A structure of the obtained yellow powder was identified with NMR.

The following 30 hydrogen signals were detected with $^1$H-NMR (CDCl$_3$). δ (ppm)=8.67 to 8.68 (2H), 8.45 (2H), 8.00 to 8.03 (2H), 7.73 to 7.87 (8H), 7.39 to 7.57 (10H).

Example 5

Synthesis of {(2-phenyl benzotriazole-5-yl) phenyl-4-yl}-bis-(biphenyl-4-yl)-amine (Compound 30)

Into a nitrogen substituted reaction vessel, 5-bromo-2-phenyl-2H-benzotriazole: 2.3 g, bis-(biphenyl-4-yl)-{4-(4,4,5,5-tetramethyl-[1,3,2] dioxaborane-2-yl)-phenyl}-amine: 5.3 g, toluene: 52 mL, and ethanol: 13 mL were added, then an aqueous solution where potassium carbonate: 3.5 g was dissolved in H$_2$O: 13 mL in advance was added, and nitrogen gas was aerated while the solution was irradiated with ultrasonic waves for 30 minutes. Tetrakistriphenyl phosphine palladium: 0.5 g was added and stirred under heated reflux for 6 hours. After standing to cool, H$_2$O was added, an organic layer was extracted by a liquid separation operation and concentrated under reduced pressure to obtain a crude product. The obtained crude product was purified by column chromatography (carrier: silica gel, eluent: toluene/n-hexane) to obtain yellow powder of {(2-phenyl benzotriazole-5-yl) phenyl-4-yl}-bis-(biphenyl-4-yl)-amine (compound 30): 3.5 g (yield: 71%).

[Chem. 24]

(Compound 30)

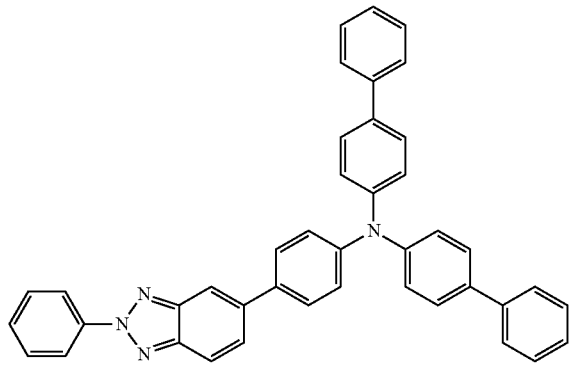

A structure of the obtained yellow powder was identified with NMR.

The following 30 hydrogen signals were detected with $^1$H-NMR (THF-$d_8$). δ (ppm)=8.41 (2H), 8.15 (1H), 7.98 (1H), 7.80 (1H), 7.72 (2H), 7.56 to 7.65 (10H), 7.47 (1H), 7.40 (4H), 7.24 to 7.29 (8H).

[Chem. 25]

(Compound 31)

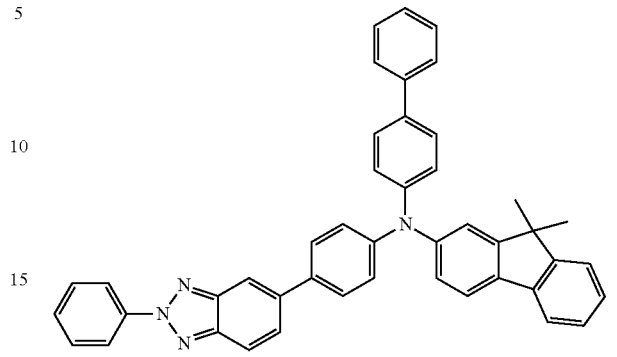

A structure of the obtained yellow powder was identified with NMR.

The following 34 hydrogen signals were detected with $^1$H-NMR (THF-$d_8$). δ (ppm)=8.41 (2H), 8.16 (1H), 7.98 (1H), 7.81 (1H), 7.72 (2H), 7.69 (2H), 7.63 (2H), 7.59 (2H), 7.58 (2H), 7.47 (1H), 7.38 to 7.43 (4H), 7.21 to 7.30 (7H), 7.12 (1H), 1.44 (6H).

Example 6

Synthesis of {(2-phenyl benzotriazole-5-yl) phenyl-4-yl}-(biphenyl-4-yl)-9,9-dimethyl-9H-fluorene-2-yl) (Compound 31)

Into a nitrogen substituted reaction vessel, 5-bromo-2-phenyl-2H-benzotriazole: 2.2 g, bis-(biphenyl-4-yl)-{4-(4,4,5,5-tetramethyl-[1,3,2]dioxaborane-2-yl)-phenyl}-amine: 5.4 g, toluene: 48 mL, and ethanol: 12 mL were added, then an aqueous solution where potassium carbonate: 3.3 g was dissolved in H$_2$O: 12 mL in advance was added, and nitrogen gas was aerated while the solution was irradiated with ultrasonic waves for 30 minutes. Tetrakistriphenyl phosphine palladium: 0.5 g was added and stirred under heated reflux for 5 hours. After standing to cool, H$_2$O was added, an organic layer was extracted by a liquid separation operation and concentrated under reduced pressure to obtain a crude product. The obtained crude product was purified by column chromatography (carrier: silica gel, eluent: toluene/n-hexane) to obtain yellow powder of {(2-phenyl benzotriazole-5-yl) phenyl-4-yl}-(biphenyl-4-yl)-9,9-dimethyl-9H-fluorene-2-yl) (compound 31): 3.9 g (yield: 77%).

Example 7

Synthesis of bis-{4-(benzotriazole-2-yl) phenyl}-{4-(naphthalene-2-yl) phenyl}amine (Compound 43)

Into a reaction vessel, 4-(naphthalen-2-yl) phenyl-amine: 5.0 g, 2-(4-bromophenyl)-2H-benzotriazole: 13.1 g, t-butoxy sodium: 6.6 g, and toluene: 130 mL were added, and nitrogen gas was aerated while the solution was irradiated with ultrasonic waves for 30 minutes. Tris(dibenzylidene acetone) dipalladium (0): 0.21 g and 2,2'-bis(diphenyl phosphino)-1,1'-binaphthyl: 0.28 g were added and stirred under heated reflux for one day. After standing to cool to 80° C., insoluble matter was filtered off, and silica gel was added to the filtrate to perform adsorption purification. Adsorbent was removed by filtration and the filtrate was concentrated to obtain a crude product. The crude product was purified by crystallization with toluene to collect a precipitated solid, to obtain yellow powder of bis-{4-(benzotriazole-2-yl) phenyl}-{4-(naphthalene-2-yl) phenyl} amine (compound 43): 6.5 g (yield: 47%).

[Chem. 26]

(Compound 43)

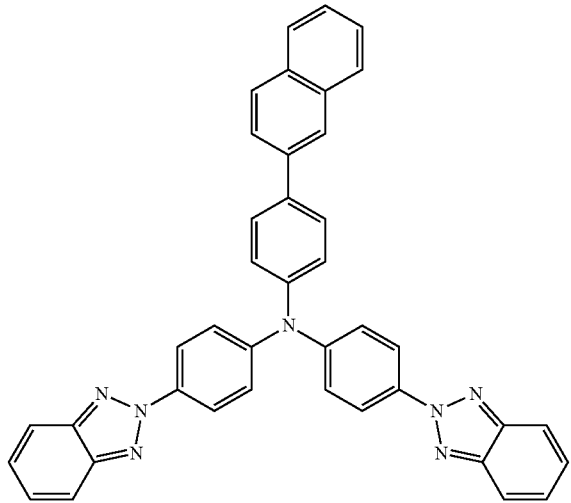

A structure of the obtained yellow powder was identified with NMR.

The following 27 hydrogen signals were detected with $^1$H-NMR (CDCl$_3$). δ (ppm)=8.33 to 8.35 (4H), 8.31 (1H), 7.73 to 7.98 (10H), 7.34 to 7.55 (12H).

[Chem. 27]

(Compound 44)

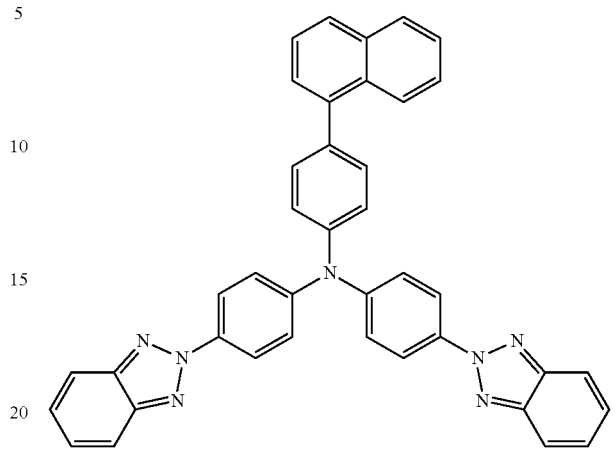

A structure of the obtained yellow powder was identified with NMR.

The following 27 hydrogen signals were detected with $^1$H-NMR (DMSO-d6). δ (ppm)=8.33 to 8.36 (4H), 7.96 to 8.06 (7H), 7.37 to 7.63 (16H).

Example 8

Synthesis of bis-{4-(benzoxazole-2-yl) phenyl}-{4-(naphthalene-1-yl) phenyl} amine (Compound 44)

Into a reaction vessel, 4-(naphthalen-1-yl) phenyl-amine: 5.0 g, 2-(4-bromophenyl)-2H-benzotriazole: 13.8 g, t-butoxy sodium: 6.6 g, and toluene: 50 mL were added, and nitrogen gas was aerated while the solution was irradiated with ultrasonic waves for 30 minutes. Tris(dibenzylidene acetone) dipalladium (0): 0.6 g and a 50% (w/v) toluene solution of tri-(t-butyl) phosphine: 0.6 mL were added and stirred under heated reflux for 8 hours. After standing to cool to 80° C., insoluble matter was filtered off, and the filtrate was concentrated to obtain a crude product. The crude product was purified by crystallization with acetone to collect a precipitated solid, to obtain yellow powder of bis-{4-(benzotriazole-2-yl) phenyl}-{4-(naphthalene-1-yl) phenyl} amine (compound 44): 6.4 g (yield: 46%).

Example 9

Synthesis of bis-{4-(benzotriazole-2-yl) phenyl}-(9,9-dimethyl-9H-fluorene-2-yl)-amine (Compound 47)

Into a reaction vessel, 9,9-dimethyl-9H-fluorene-2-yl-amine: 3.8 g, 2-(4-bromophenyl)-2H-benzotriazole: 10.9 g, t-butoxy sodium: 5.2 g, and toluene: 40 mL were added, and nitrogen gas was aerated while the solution was irradiated with ultrasonic waves for 30 minutes. Tris(dibenzylidene acetone) dipalladium (0): 0.5 g and a 50% (w/v) toluene solution of tri-(t-butyl) phosphine: 0.44 mL were added and stirred under heated reflux for 7 hours. Toluene was added to perform dispersion washing, insoluble matter was thermal-filtered off, and the filtrate was concentrated to obtain a crude product. The crude product was purified by crystallization with a toluene/methanol mixed solvent to collect a precipitated solid, to obtain yellow powder of bis-{4-(benzotriazole-2-yl) phenyl}-(9,9-dimethyl-9H-fluorene-2-yl)-amine (compound 47): 6.8 g (yield: 63%).

[Chem. 28]

(Compound 47)

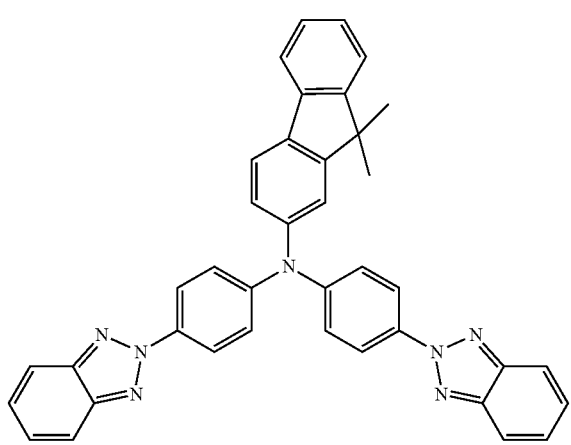

[Chem. 29]

(Compound 48)

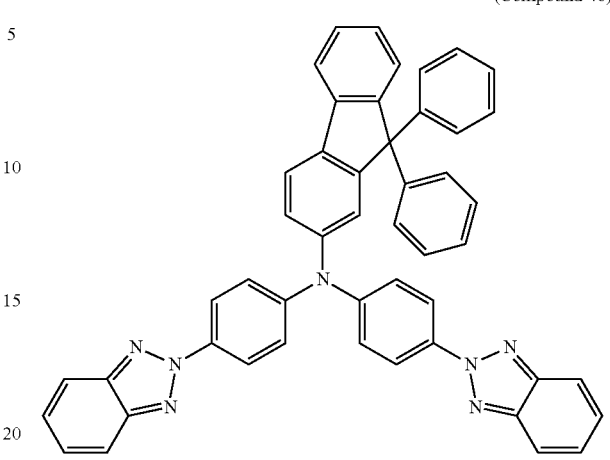

A structure of the obtained yellow powder was identified with NMR.

The following 28 hydrogen signals were detected with $^1$H-NMR (DMSO-d6). δ (ppm)=8.29 to 8.31 (4H), 8.01 to 8.04 (4H), 7.81 to 7.90 (2H), 7.19 to 7.56 (13H), 1.43 (6H).

A structure of the obtained yellow powder was identified with NMR.

The following 32 hydrogen signals were detected with $^1$H-NMR (DMSO-d6). δ (ppm)=8.24 to 8.27 (4H), 7.91 to 8.04 (6H), 7.40 to 7.54 (6H), 7.23 to 7.34 (12H), 7.09 to 7.12 (4H).

Example 10

Synthesis of bis-{4-(benzoxazole-2-yl) phenyl}-(9,9-diphenyl-9H-fluorene-2-yl)-amine (Compound 48)

Into a reaction vessel, 9,9-diphenyl-9H-fluorene-2-yl-amine: 5.0 g, 2-(4-bromophenyl)-2H-benzotriazole: 9.0 g, t-butoxy sodium: 4.3 g, and toluene: 60 mL were added, and nitrogen gas was aerated while the solution was irradiated with ultrasonic waves for 30 minutes. Tris(dibenzylidene acetone) dipalladium (0): 0.4 g and a 50% (w/v) toluene solution of tri-(t-butyl) phosphine: 0.4 mL were added and stirred under heated reflux for 7 hours. After standing to cool, toluene was added to perform dispersion washing, insoluble matter was filtered off, and the filtrate was concentrated to obtain a crude product. The crude product was purified by crystallization with toluene to collect a precipitated solid, to obtain yellow powder of bis-{4-(benzoxazole-2-yl) phenyl}-(9,9-diphenyl-9H-fluorene-2-yl)-amine (compound 48): 8.1 g (yield: 75%).

Example 11

Synthesis of {3-(benzotriazole-2-yl) phenyl}-bis (biphenyl-4-yl)-amine (Compound 68)

Into a reaction vessel, 2-(3-bromophenyl)-2H-benzotriazole: 9.6 g, bis-(biphenyl-4-yl)-amine: 9.0 g, t-butoxy sodium: 4.3 g, and toluene: 150 mL were added, and nitrogen gas was aerated while the solution was irradiated with ultrasonic waves for 30 minutes. Palladium (II) acetate: 0.1 g and a 50% (w/v) toluene solution of tri-(t-butyl) phosphine: 0.24 mL were added and stirred under heated reflux for 2 hours. After standing to cool, toluene was added to perform dispersion washing, insoluble matter was filtered off, and silica gel and active white clay were added to the filtrate to perform adsorption purification. Adsorbent was removed by filtration and the filtrate was concentrated to obtain a crude product. The crude product was purified by crystallization with a toluene/acetone mixed solvent to collect a precipitated solid, to obtain yellow powder of {3-(benzotriazole-2-yl) phenyl}-bis(biphenyl-4-yl)-amine (compound 68): 8.2 g (yield: 53%).

[Chem. 30]

(Compound 68)

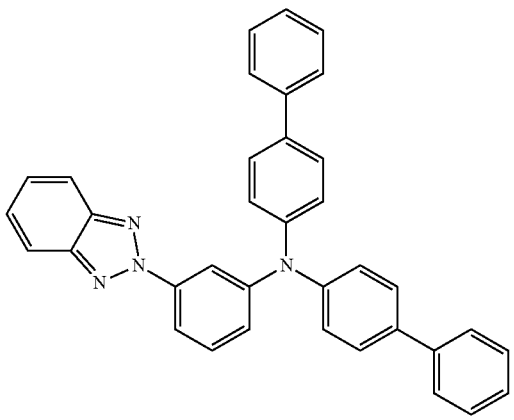

Example 12

Synthesis of bis-{3-(benzotriazole-2-yl) phenyl}-{4-(naphthalene-2-yl) phenyl} amine (Compound 77)

Into a reaction vessel, 4-(naphthalen-2-yl) phenyl-amine: 6.1 g, 2-(3-bromophenyl)-2H-benzotriazole: 16.0 g, t-butoxy sodium: 8.0 g, and toluene: 170 mL were added, and nitrogen gas was aerated while the solution was irradiated with ultrasonic waves for 30 minutes. Tris(dibenzylidene acetone) dipalladium (0): 0.25 g and 2,2'-bis(diphenyl phosphino)-1,1'-binaphthyl: 0.35 g were added and stirred under heated reflux for one night. After adding toluene and standing to cool to 80° C., insoluble matter was filtered off, and silica gel was added to the filtrate to perform adsorption purification. Adsorbent was removed by filtration and the filtrate was concentrated to obtain a crude product. The crude product was purified by crystallization with toluene to collect a precipitated solid, to obtain yellow powder of bis-{3-(benzotriazole-2-yl) phenyl}-{4-(naphthalene-2-yl) phenyl} amine (compound 77): 6.2 g (yield: 37%).

[Chem. 31]

(Compound 77)

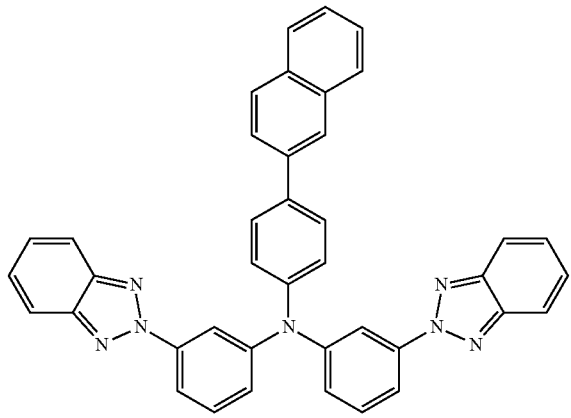

A structure of the obtained yellow powder was identified with NMR.

The following 27 hydrogen signals were detected with $^1$H-NMR (CDCl$_3$). δ (ppm)=8.24 to 8.25 (2H), 8.08 to 8.11 (3H), 7.89 to 7.96 (7H), 7.72 to 7.81 (3H), 7.30 to 7.55 (12H).

Example 13

Synthesis of tris-(4-benzotriazole-2-yl-phenyl)-amine (Compound 85)

Into a reaction vessel, 4-benzotriazole-2-yl-phenyl amine: 2.5 g, t-butoxy sodium: 3.4 g, and toluene: 60 mL were added, and nitrogen gas was aerated while the solution was irradiated with ultrasonic waves for 30 minutes. Tris(dibenzylidene acetone) dipalladium (0): 0.2 g and a 50% (w/v) toluene solution of tri-(t-butyl) phosphine: 0.5 mL were added and stirred under heated reflux for one night. Toluene was added to perform dispersion washing, insoluble matter was thermal-filtered off, and the filtrate was concentrated to obtain a crude product. The obtained crude product was purified by column chromatography (carrier: silica gel, eluent: toluene/n-hexane) to obtain yellow powder of tris-(4-benzotriazole-2-yl-phenyl)-amine (compound 85): 3.3 g (yield: 46.5%).

[Chem. 32]

(Compound 85)

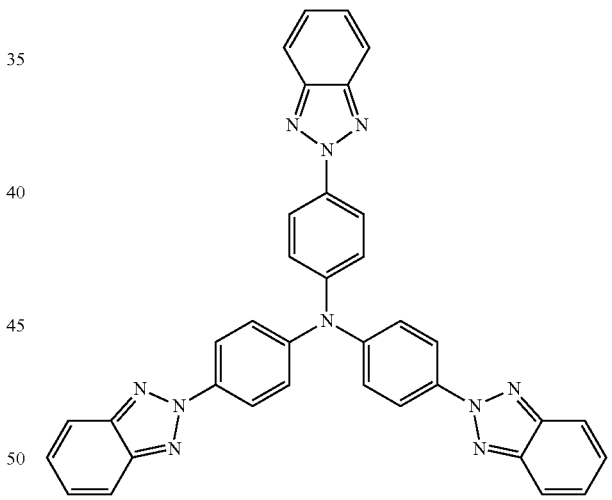

A structure of the obtained yellow powder was identified with NMR.

The following 24 hydrogen signals were detected with $^1$H-NMR (CDCl$_3$). δ (ppm)=8.26 (6H), 7.93 (6H), 7.42 (6H), 7.33 (6H).

Example 14

A melting point and a glass transition point of each of the benzazole compounds represented by the general formula (A-1) were measured with a high sensitivity differential scanning calorimeter (DSC 3100 SA manufactured by Bruker AXS GmbH).

|  | Melting point | Glass transition point |
| --- | --- | --- |
| Compound of Example 1 | 207° C. | 102° C. |
| Compound of Example 2 | 187° C. | 100° C. |
| Compound of Example 3 | not observed | 101° C. |
| Compound of Example 4 | not observed | 106° C. |
| Compound of Example 5 | 109° C. | 100° C. |
| Compound of Example 6 | 125° C. | 106° C. |
| Compound of Example 7 | 271° C. | 110° C. |
| Compound of Example 8 | 224° C. | 113° C. |
| Compound of Example 9 | 228° C. | 119° C. |
| Compound of Example 10 | 267° C. | 146° C. |
| Compound of Example 11 | not observed | 100° C. |
| Compound of Example 12 | not observed | 105° C. |
| Compound of Example 13 | not observed | 117° C. |

The compounds having a benzazole ring structure represented by the general formula (A-1) have a glass transition point of 100° C. or higher, which indicates that the thin film state is stable.

Example 15

A deposited film having a film thickness of 80 nm was produced on a silicon substrate by using the amine compound having a benzazole ring structure represented by the general formula (A-1), and a refractive index n and an extinction coefficient k at wavelengths of 400 nm and 410 nm were measured with a spectroscopic measurement device (F10-RT-UV manufactured by Filmetrics Japan, Inc.). For comparison, a comparative compound (2-1) and Alq$_3$ of the following structural formulae were also measured (see, for example, Patent Literature 4). Measurement results were summarized in Table 1.

[Chem. 33]

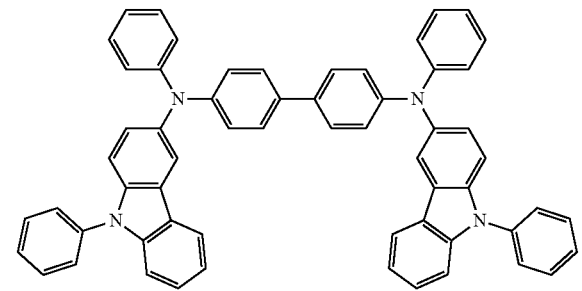

Comparative Compound (2-1)

[Chem. 34]

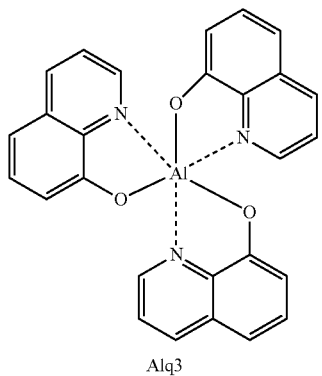

Alq3

TABLE 1

|  | Refractive index n (λ: 400 nm) | Refractive index n (λ: 410 nm) | Extinction coefficient k (λ: 400 nm) | Extinction coefficient k (λ: 410 nm) |
| --- | --- | --- | --- | --- |
| Compound 17 | 2.30 | 2.27 | 0.33 | 0.25 |
| Compound 6 | 2.35 | 2.29 | 0.50 | 0.30 |
| Compound 7 | 2.30 | 2.24 | 0.49 | 0.31 |
| Compound 23 | 2.41 | 2.30 | 0.45 | 0.30 |
| Compound 30 | 2.29 | 2.20 | 0.33 | 0.22 |
| Compound 31 | 2.28 | 2.20 | 0.33 | 0.20 |
| Compound 43 | 2.37 | 2.47 | 0.70 | 0.47 |
| Compound 44 | 2.33 | 2.40 | 0.67 | 0.45 |
| Compound 47 | 2.30 | 2.39 | 0.65 | 0.40 |
| Compound 48 | 2.35 | 2.42 | 0.68 | 0.40 |
| Compound 68 | 2.15 | 2.13 | 0.28 | 0.24 |
| Compound 77 | 2.20 | 2.15 | 0.28 | 0.25 |
| Compound 85 | 2.50 | 2.43 | 0.88 | 0.56 |
| Comparative compound (2-1) | 2.13 | 2.10 | 0.15 | 0.06 |
| Alq$_3$ | 1.86 | 1.89 | 0.16 | 0.14 |

Thus, the compounds of the present example have a refractive index of a value equal to or higher than that of the comparative compound (2-1) and Alq$_3$, and improvement in light extraction efficiency in the organic EL device can be expected. The extinction coefficient at a wavelength of 400 nm to 410 nm was larger than the extinction coefficient at a wavelength of 410 nm. While the extinction coefficient at a wavelength of 400 nm to 410 nm of the comparative compound (2-1) and Alq$_3$ is less than 0.20, the compounds of the present example have a large value, which indicates that light at a wavelengths of 400 nm to 410 nm among sunlight is well absorbed and does not affect a material inside the device.

Example 16

The compounds of the present example were adjusted as a toluene solution at a concentration of $1.0 \times 10^{-5}$ mol/L to measure absorbance of the solution at wavelengths of 400 nm and 410 nm. An absorption coefficient was calculated from a calibration curve of absorbance at a peak wavelength by adjusting a concentration of the toluene solution to four kinds of concentration of $5.0 \times 10^{-6}$ mol/L, $1.0 \times 10^{-5}$ mol/L, $1.5 \times 10^{-5}$ mol/L, and $2.0 \times 10^{-5}$ mol/L and measuring the absorbance with an ultraviolet-visible near-infrared spectrophotometer (V-650 manufactured by JASCO Corporation). For comparison, the comparative compound (2-1) and Alq$_3$ of the above-mentioned structural formulae were also measured. Measurement results were summarized in Table 2.

TABLE 2

|  | Peak wavelength ($\lambda_{max}$) | Absorbance (λ: 400 nm) | Absorbance (λ: 410 nm) | Absorption coefficient |
| --- | --- | --- | --- | --- |
| Compound 17 | 380 nm | 0.50 | 0.20 | 94400 |
| Compound 6 | 374 nm | 0.81 | 0.30 | 123605 |
| Compound 7 | 370 nm | 0.79 | 0.25 | 112990 |
| Compound 23 | 355 nm | 0.66 | 0.27 | 124458 |
| Compound 30 | 349 nm | 0.60 | 0.22 | 124960 |
| Compound 31 | 345 nm | 0.60 | 0.23 | 122199 |
| Compound 43 | 377 nm | 0.85 | 0.30 | 149105 |

TABLE 2-continued

| | Peak wavelength ($\lambda_{max}$) | Absorbance ($\lambda$: 400 nm) | Absorbance ($\lambda$: 410 nm) | Absorption coefficient |
|---|---|---|---|---|
| Compound 44 | 370 nm | 0.77 | 0.29 | 141650 |
| Compound 47 | 370 nm | 0.70 | 0.25 | 134470 |
| Compound 48 | 373 nm | 0.72 | 0.25 | 129256 |
| Compound 68 | 305 nm | 0.45 | 0.22 | 104014 |
| Compound 77 | 310 nm | 0.50 | 0.20 | 112015 |
| Compound 85 | 385 nm | 0.87 | 0.44 | 168087 |
| Comparative compound (2-1) | 358 nm | 0.07 | 0.02 | 48856 |
| Alq$_3$ | 394 nm | 0.07 | 0.06 | 7518 |

In an absorption spectrum, the absorbance at a wavelength of 400 nm to 410 nm was larger than the absorbance at a wavelength of 410 nm. In this way, while the absorbance at a wavelength of 400 nm to 410 nm of the comparative compound (2-1) and Alq$_3$ is 0.10 or less, the compounds of the present example have a large value of 0.20 or more, which indicates that light at a wavelength of 400 nm to 410 nm among sunlight is well absorbed. In addition, as compared with the comparative compound (2-1) and Alq$_3$, the compounds of the present example have a large value of absorption coefficient, and light is well absorbed under the same concentration condition. With respect to the thin film, it can be found that the more the film thickness is, the better light is absorbed, and the material is excellent in light resistance.

Example 17

As illustrated in FIG. 1, the organic EL device was produced by depositing a hole injection layer 3, a hole transport layer 4, a light emitting layer 5, an electron transport layer 6, an electron injection layer 7, a cathode 8, and a capping layer 9 in this order on a preformed reflective ITO electrode as a metal anode 2 on a glass substrate 1.

Specifically, the glass substrate 1 on which ITO having a film thickness of 50 nm, a reflective film of a silver alloy having a film thickness of 100 nm and ITO having a film thickness of 5 nm were formed in order was subjected to ultrasonic washing in isopropyl alcohol for 20 minutes, and then dried for 10 minutes on a hot plate heated to 250° C. Then, after performing a UV ozone treatment for 2 minutes, the glass substrate with ITO was mounted in a vacuum deposition machine and depressurized to 0.001 Pa or less. Next, as the hole injection layer 3 to cover the transparent anode 2, an electron acceptor (Acceptor-1) of the following structural formula and a compound (3-1) of the following structural formula were subjected to binary deposition at a deposition rate where a ratio of deposition rates of Acceptor-1:Compound (3-1)=3:97 to form the hole injection layer 3 so as to have a film thickness of 10 nm. A layer of the compound (3-1) of the following structural formula was formed to have a film thickness of 140 nm as the hole transport layer 4 on the hole injection layer 3. A compound (3-2) of the following structural formula and a compound (3-3) of the following structural formula as the light emitting layer 5 were subjected to binary deposition at a deposition rate where a ratio of deposition rates of (3-2):(3-3)=5:95 on the hole transport layer 4 to form the light emitting layer 5 so as to have a film thickness of 20 nm. A compound (3-4) of the following structural formula and a compound (3-5) of the following structural formula as the electron transport layer 6 were subjected to binary deposition at a deposition rate where a ratio of deposition rates of (3-4):(3-5)=50:50 on the light emitting layer 5 to form the electron transport layer 6 so as to have a film thickness of 30 nm. A layer of lithium fluoride was formed to have a film thickness of 1 nm as the electron injection layer 7 on the electron transport layer 6.

A layer of a magnesium silver alloy was formed to have a film thickness of 12 nm as the cathode 8 on the electron injection layer 7. Finally, a layer of the compound 17 of Example 1 was formed to have a film thickness of 60 nm as the capping layer 9. The produced organic EL device was subjected to characteristic measurement in the atmosphere at room temperature.

Table 3 summarized measurement results of light emitting characteristics in which a direct current voltage was applied to the produced organic EL device.

[Chem. 35]

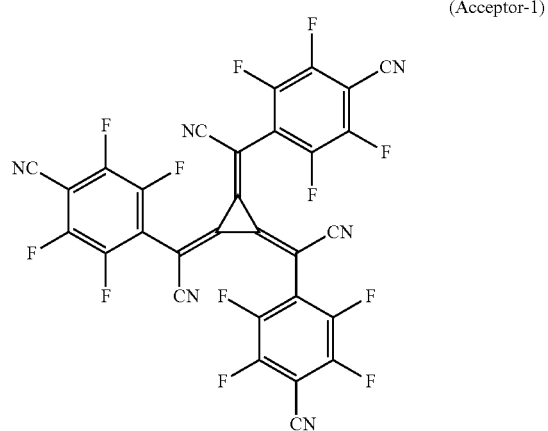

(Acceptor-1)

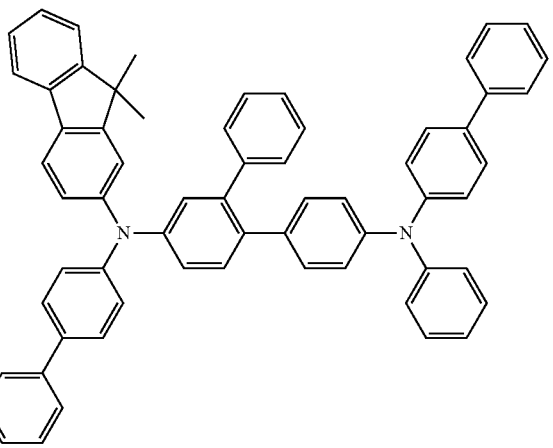

(3-1)

-continued (3-2)

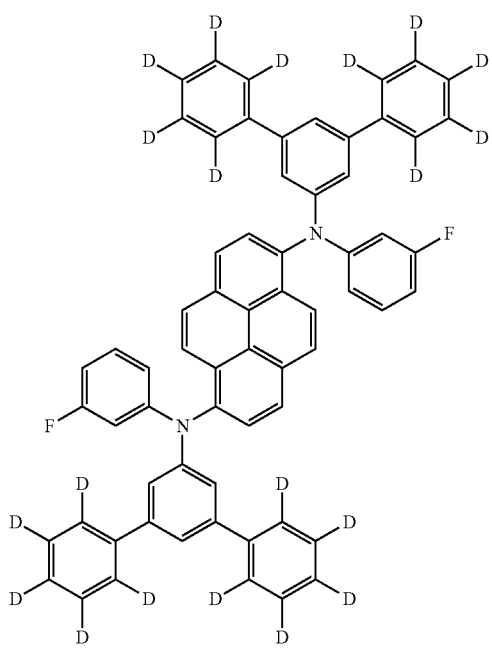

(3-3)

(3-4)

(3-5)

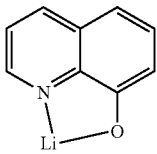

Example 18

The organic EL device was produced under the same conditions as in Example 17 except that the compound 6 of Example 2 was used in place of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 19

The organic EL device was produced under the same conditions as in Example 17 except that the compound 7 of Example 3 was used in place of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 20

The organic EL device was produced under the same conditions as in Example 17 except that the compound 23 of Example 4 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 21

The organic EL device was produced under the same conditions as in Example 17 except that the compound 30 of Example 5 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 22

The organic EL device was produced under the same conditions as in Example 17 except that the compound 31 of Example 6 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 23

The organic EL device was produced under the same conditions as in Example 17 except that the compound 43 of Example 7 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 24

The organic EL device was produced under the same conditions as in Example 17 except that the compound 44 of Example 8 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 25

The organic EL device was produced under the same conditions as in Example 17 except that the compound 47 of Example 9 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 26

The organic EL device was produced under the same conditions as in Example 17 except that the compound 48 of Example 10 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 27

The organic EL device was produced under the same conditions as in Example 17 except that the compound 68 of Example 11 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 28

The organic EL device was produced under the same conditions as in Example 17 except that the compound 77 of Example 12 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Example 29

The organic EL device was produced under the same conditions as in Example 17 except that the compound 85 of Example 13 was used instead of the compound 17 of Example 1 as the material of the capping layer 9. The produced organic EL device was subjected to characteristic measurement in the atmosphere at room temperature. Measurement results of light emitting characteristics when a direct current voltage was applied to the produced organic EL device were summarized in Table 3.

Comparative Example 1

For comparison, an organic EL device was produced under the same conditions as in Example 17 except that a layer of the comparative compound (2-1) of the above-mentioned structural formula was formed to have a film thickness of 60 nm instead of the compound 17 of Example 1 as the capping layer 9. The produced organic EL device was subjected to characteristic measurement in the atmosphere at room temperature. Table 3 summarized measurement results of light emitting characteristics in which a direct current voltage was applied to the produced organic EL device.

Comparative Example 2

For comparison, an organic EL device was produced under the same conditions as in Example 17 except that a layer of Alq$_3$ was formed to have a film thickness of 60 nm instead of the compound 17 of Example 1 as the capping layer 9. The produced organic EL device was subjected to characteristic measurement in the atmosphere at room temperature. Table 3 summarized measurement results of light emitting characteristics in which a direct current voltage was applied to the produced organic EL device.

Table 3 summarized results of measuring a device lifetime by using the organic EL devices produced in Examples 17 to 29 and Comparative Examples 1 and 2. The device lifetime was measured as time until decay to 95% decay when initial luminance was 100% when constant current driving was performed at 10 mA/cm$^2$.

TABLE 3

| | Capping layer | Voltage [V] (@10 mA/cm$^2$) | Luminance [cd/m$^2$] (@10 mA/cm$^2$) | Luminous efficiency [cd/A] (@10 A/cm$^2$) | Power Efficiency [lm/W] (@10 A/cm$^2$) | Device lifetime 95% decay |
|---|---|---|---|---|---|---|
| Example 17 | Compound 17 | 3.66 | 685 | 6.90 | 5.92 | 163 hours |
| Example 18 | Compound 6 | 3.66 | 700 | 7.00 | 6.01 | 165 hours |
| Example 18 | Compound 7 | 3.65 | 697 | 6.97 | 6.01 | 161 hours |
| Example 20 | Compound 23 | 3.66 | 681 | 6.81 | 5.85 | 158 hours |
| Example 21 | Compound 30 | 3.66 | 675 | 6.75 | 5.79 | 155 hours |
| Example 22 | Compound 31 | 3.64 | 675 | 6.75 | 5.83 | 154 hours |
| Example 23 | Compound 43 | 3.65 | 715 | 7.15 | 6.15 | 159 hours |
| Example 24 | Compound 44 | 3.65 | 711 | 7.11 | 6.12 | 163 hours |
| Example 25 | Compound 47 | 3.64 | 706 | 7.06 | 6.09 | 160 hours |
| Example 26 | Compound 48 | 3.64 | 708 | 7.08 | 6.11 | 160 hours |
| Example 27 | Compound 68 | 3.64 | 674 | 6.74 | 5.82 | 156 hours |
| Example 28 | Compound 77 | 3.64 | 684 | 6.84 | 5.90 | 151 hours |
| Example 29 | Compound 85 | 3.64 | 722 | 7.22 | 6.23 | 164 hours |
| Comparative Example 1 | Comparative compound (2-1) | 3.69 | 668 | 6.68 | 5.68 | 121 hours |
| Comparative Example 2 | Alq$_3$ | 3.67 | 647 | 6.47 | 5.54 | 106 hours |

As shown in Table 3, a drive voltage at a current density of 10 mA/cm$^2$ is almost the same as the devices of Comparative Example 1 and Comparative Example 2 and the devices of Examples 17 to 29. On the other hand, luminance, luminous efficiency, power efficiency, and lifetime were improved in the devices of Examples 17 to 29 with respect to the devices of Comparative Example 1 and Comparative Example 2. This indicates that the light extraction efficiency can be greatly improved since the capping layer contains the material of the present example, which is suitably used for the organic EL device and has a high refractive index.

Although the present invention has been described in detail with reference to specific embodiments, it is apparent to those skilled in the art that it is possible to add various alterations and modifications without departing from the spirit and the scope of the present invention.

The present application is based on Japanese Patent Application (No. 2018-001564) filed on Jan. 10, 2018, the entirety of which is incorporated by reference. In addition, all references cited here are entirely incorporated.

INDUSTRIAL APPLICABILITY

As described above, the amine compound having a benzazole ring structure represented by the general formula (A-1) that is suitably used in the organic EL device of the present invention has a high light absorption coefficient and a high refractive index, can greatly improve light extraction efficiency, and is stable in a thin film state, and thus is excellent as a compound for the organic EL device. By producing the organic EL device using the compound, high efficiency can be obtained, and durability or light resistance can be improved so as to absorb light of sunlight and not to influence the material inside the device. Use of the compound that does not have absorption in respective wavelength ranges of blue, green and red is particularly suitable when it is desired to display a vivid and bright image with good color purity. For example, it is possible to develop a home electrical appliance or a lighting application.

REFERENCE SIGN LIST

1 Glass substrate
2 Transparent anode
3 Hole injection layer
4 Hole transport layer
5 Light emitting layer
6 Electron transport layer
7 Electron injection layer
8 Cathode
9 Capping layer

The invention claimed is:

1. An organic EL device having at least an anodic electrode, a hole transport layer, a light emitting layer, an electron transport layer, a cathodic electrode, and a capping layer in this order, wherein the capping layer comprises an amine compound having a benzazole ring structure represented by the following general formula (A-1):

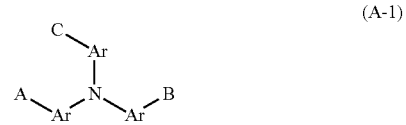

(A-1)

(in the formula, A represents a monovalent group represented by the following general formula (B-1) where one position in R1 to R6 is a bonding site; B and C may be the same as or different from each other, and each represents a monovalent group represented by the following general formula (B-1) where one position in R1 to R6 is a bonding site, a substituted or unsubstituted aromatic hydrocarbon group, a substituted or unsubstituted aromatic heterocyclic group, or a substituted or unsubstituted condensed polycyclic aromatic group; Ar's may be the same as or different from each other, and each represents a divalent group of a substituted or unsubstituted aromatic hydrocarbon group, a substituted or unsubstituted aromatic heterocyclic group, or a substituted or unsubstituted condensed polycyclic aromatic group, or a single bond; and two Ar's that are adjacent to each other via a nitrogen atom may be bonded together by a single bond, a substituted or unsubstituted methylene group, an oxygen atom, or a sulfur atom to form a ring);

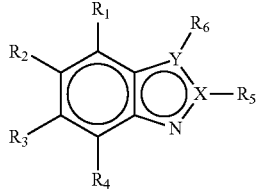

(B-1)

(in the formula, R1 to R6 may be the same as or different from each other, and each represents a linking group as a bonding site that connects to Ar, a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; and X and Y represent a carbon atom or a nitrogen atom, provided that in a case where X and Y are nitrogen atoms, X or Y does not have $R^5$ or $R^6$, and a case where X and Y are carbon atoms is excepted);

provided that when B or C is said substituted aromatic hydrocarbon group, said substituted aromatic heterocyclic group, or said substituted condensed polycyclic aromatic group, then the substituent is selected from the group consisting of a deuterium atom, a cyano group, a nitro group, a halogen atom, a silyl group, a linear or branched alkyl group having a carbon number of 1 to 6, a linear or branched alkyloxy group having a carbon number of 1 to 6, an alkenyl group, an aryloxy group, an aryl alkyloxy group, an aromatic hydrocarbon group, a condensed polycyclic aromatic group, an aryl group having a carbon number of 6 to 30 and a heteroaryl group having a carbon number of 2 to 20; and provided that when Ar is said substituted aromatic hydrocarbon group, said substituted aromatic heterocyclic group, or said substituted condensed polycyclic aromatic group, then the substituent is selected from the group consisting of a deuterium atom, a cyano group, a nitro group, a halogen atom, a silyl group, a linear or branched alkyl group having a carbon number of 1 to 6, a linear or branched alkyloxy group having a carbon number of 1 to 6, an alkenyl group, an aryloxy group, an aryl alkyloxy group, an aromatic hydrocarbon group, a condensed polycyclic aromatic group, an aryl group having a carbon number of 6 to 30 and a heteroaryl group having a carbon number of 2 to 20.

2. The organic EL device according to claim 1, wherein the amine compound having a benzazole ring structure has an extinction coefficient of 0.20 or more at a wavelength of 400 nm to 410 nm and has an absorbance of 0.20 or more at a wavelength of 400 nm to 410 nm in an absorption spectrum of a toluene solution with a concentration of $1.0 \times 10^{-5}$ mol/L.

3. The organic EL device according to claim 1, wherein the general formula (B-1) is represented by the following general formula (B-2) or (B-3):

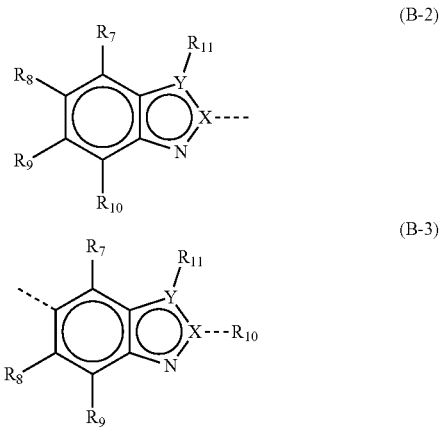

(in the formulae, a broken line is a bonding site; R7 to R11 may be the same as or different from each other, and each represents a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group; and X and Y represent a carbon atom or a nitrogen atom, provided that in a case where X and Y are nitrogen atoms, Y does not have R11, and a case where X and Y are carbon atoms is excepted); and provided that when one or more of R7 to R11 is said linear or branched alkyl group having a carbon number of 1 to 6 having a substituent, said cycloalkyl group having a carbon number of 5 to 10 having a substituent, said linear or branched alkenyl group having a carbon number of 2 to 6 having a substituent, said linear or branched alkyloxy group having a carbon number of 1 to 6 having a substituent, said cycloalkyloxy group having a carbon number of 5 to 10 having a substituent, said substituted aromatic hydrocarbon group, said substituted aromatic heterocyclic group, said substituted condensed polycyclic aromatic group, or said substituted or unsubstituted aryloxy group, then the substituent is selected from the group consisting of a deuterium atom, a cyano group, a nitro group, a halogen atom, a silyl group, a linear or branched alkyl group having a carbon number of 1 to 6, a linear or branched alkyloxy group having a carbon number of 1 to 6, an alkenyl group, an aryloxy group, an aryl alkyloxy group, an aromatic hydrocarbon group, a condensed polycyclic aromatic group, an aryl group having a carbon number of 6 to 30 and a heteroaryl group having a carbon number of 2 to 20.

4. The organic EL device according to claim 1, wherein the general formula (B-1) is represented by the following general formula (B-4) or (B-5):

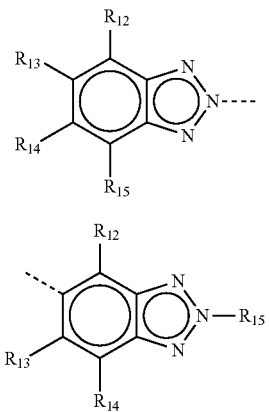

(in the formulae, a broken line is a bonding site; R12 to R15 may be the same as or different from each other, and each represents a hydrogen atom, a deuterium atom, a fluorine atom, a chlorine atom, a cyano group, a nitro group, a linear or branched alkyl group having a carbon number of 1 to 6 which may have a substituent, a cycloalkyl group having a carbon number of 5 to 10 which may have a substituent, a linear or branched alkenyl group having a carbon number of 2 to 6 which may have a substituent, a linear or branched alkyloxy group having a carbon number of 1 to 6 which may have a substituent, a cycloalkyloxy group having a carbon number of 5 to 10 which may have a substituent, a substituted or unsubstituted aromatic hydrocarbon group, a substituted or unsubstituted aromatic heterocyclic group, a substituted or unsubstituted condensed polycyclic aromatic group, or a substituted or unsubstituted aryloxy group); and provided that when one or more of R12 to R15 is said linear or branched alkyl group having a carbon number of 1 to 6 having a substituent, said cycloalkyl group having a carbon number of 5 to 10 having a substituent, said linear or branched alkenyl group having a carbon number of 2 to 6 having a substituent, said linear or branched alkyloxy group having a carbon number of 1 to 6 having a substituent, said cycloalkyloxy group having a carbon number of 5 to 10 having a substituent, said substituted aromatic hydrocarbon group, said substituted aromatic heterocyclic group, said substituted condensed polycyclic aromatic group, or said substituted aryloxy group, then the substituent is selected from the group consisting of a deuterium atom, a cyano group, a nitro group, a halogen atom, a silyl group, a linear or branched alkyl group having a carbon number of 1 to 6, a linear or branched alkyloxy group having a carbon number of 1 to 6, an alkenyl group, an aryloxy group, an aryl alkyloxy group, an aromatic hydrocarbon group, a condensed polycyclic aromatic group, an aryl group having a carbon number of 6 to 30 and a heteroaryl group having a carbon number of 2 to 20.

5. The organic EL device according to claim 1, wherein A, B and C each have a benzazole ring structure in the general formula (A-1).

6. The organic EL device according to claim 1, wherein in the general formula (A-1), A and B each have a benzazole ring structure, and C represents a substituted or unsubstituted aromatic hydrocarbon group, a substituted or unsubstituted aromatic heterocyclic group, or a substituted or unsubstituted condensed polycyclic aromatic group.

7. The organic EL device according to claim 1, wherein in the general formula (A-1), A has a benzazole ring structure, and
B and C each represents a substituted or unsubstituted aromatic hydrocarbon group, a substituted or unsubstituted aromatic heterocyclic group, or a substituted or unsubstituted condensed polycyclic aromatic group.

8. The organic EL device according to claim 5, wherein A, B and C are the same as each other in the general formula (A-1).

9. The organic EL device according to claim 5, wherein A and B are the same as each other in the general formula (A-1).

10. The organic EL device according to claim 5, wherein A, B and C are not the same as each other in the general formula (A-1).

11. The organic EL device according to claim 5, wherein A and B are not the same as each other in the general formula (A-1).

12. The organic EL device according to claim 1, wherein the capping layer has a thickness in a range of 30 nm to 120 nm.

13. The organic EL device according to claim 1, wherein the capping layer has a refractive index of 1.85 or more with respect to light having a wavelength in a range of 400 nm to 410 nm.

* * * * *